US012648781B2

(12) United States Patent
Nachmias et al.

(10) Patent No.: US 12,648,781 B2
(45) Date of Patent: Jun. 9, 2026

(54) OFFSET GUIDING DEVICE AND METHOD OF USE THEREOF

(71) Applicant: T.A.G. Medical Devices-Agriculture Cooperative Ltd., Kibbutz Gaaton (IL)

(72) Inventors: Shai Nachmias, Nahariya (IL); Dror Biton, Karmiel (IL); Uri Gabel, Massad (IL); Hagay Botansky, Haifa (IL)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 205 days.

(21) Appl. No.: 18/268,347

(22) PCT Filed: Dec. 20, 2021

(86) PCT No.: PCT/IL2021/051509
§ 371 (c)(1),
(2) Date: Jun. 20, 2023

(87) PCT Pub. No.: WO2022/130392
PCT Pub. Date: Jun. 23, 2022

(65) Prior Publication Data
US 2024/0065709 A1 Feb. 29, 2024

Related U.S. Application Data

(60) Provisional application No. 63/128,117, filed on Dec. 20, 2020.

(51) Int. Cl.
*A61B 17/17* (2006.01)
*A61B 17/15* (2006.01)
(Continued)

(52) U.S. Cl.
CPC ........ *A61B 17/1767* (2013.01); *A61B 17/158* (2013.01); *A61B 17/8866* (2013.01); (Continued)

(58) Field of Classification Search
CPC .............. A61B 17/1767; A61B 17/158; A61B 17/1677; A61B 17/8866
See application file for complete search history.

(56) References Cited

U.S. PATENT DOCUMENTS 4,813,407 A * 3/1989 Vogen .................... A61B 17/29
606/86 R
4,848,327 A 7/1989 Perdue
(Continued)

FOREIGN PATENT DOCUMENTS

CN 207024114 2/2023
JP 51-32093 3/1976
(Continued)

OTHER PUBLICATIONS

International Search Report and the Written Opinion Dated May 15, 2022 From the International Searching Authority Re. Application No. PCT/IL21/51509. (18 Pages).
(Continued)

*Primary Examiner* — Matthew J Lawson

(57) ABSTRACT
A bone drill guiding device, comprising: a drill entry portion including a first contact point for engaging a first side of a bone, wherein the drill entry portion includes at least one bore sized to receive a bone drill therethrough; a bone securing portion including a second contact point for engaging a second side of the bone, the second side of the bone opposite the first side of the bone; wherein the device includes a third contact point on one of the drill entry portion and the bone securing portion; and a coupling to selectably rigidly connect the drill entry portion and the bone securing portion for positioning the drill entry portion and the bone securing portion on opposite sides of the bone.

19 Claims, 32 Drawing Sheets

(51) Int. Cl.

| | |
|---|---|
| *A61B 17/16* | (2006.01) |
| *A61B 17/88* | (2006.01) |
| *A61B 17/00* | (2006.01) |
| *A61B 90/00* | (2016.01) |

(52) U.S. Cl.
CPC ................. *A61B 2017/0046* (2013.01); *A61B 2017/00738* (2013.01); *A61B 17/1677* (2013.01); *A61B 2090/3962* (2016.02)

(56) References Cited

U.S. PATENT DOCUMENTS

| | | | | |
|---|---|---|---|---|
| 5,330,468 | A | 7/1994 | Burkhart | |
| 5,643,273 | A | 7/1997 | Clark | |
| 5,733,289 | A * | 3/1998 | Seedhom | A61B 17/1677 606/80 |
| 5,885,298 | A * | 3/1999 | Herrington | A61B 17/1767 606/88 |
| 6,010,509 | A * | 1/2000 | Delgado | A61F 2/461 606/88 |
| 7,344,540 | B2 * | 3/2008 | Smucker | A61B 17/1677 606/87 |
| 8,236,001 | B2 * | 8/2012 | Willi | A61B 17/175 606/89 |
| 8,747,410 | B2 * | 6/2014 | Claypool | A61B 17/158 606/88 |
| 9,198,676 | B2 | 12/2015 | Pilgeram et al. | |
| 10,022,138 | B2 | 7/2018 | Wong | |
| 10,512,475 | B2 | 12/2019 | Lizardi | |
| 2006/0142777 | A1 * | 6/2006 | Bastian | A61B 17/158 606/88 |
| 2006/0195108 | A1 | 8/2006 | Fox | |
| 2008/0097450 | A1 * | 4/2008 | Brown | A61B 17/158 606/88 |
| 2008/0103506 | A1 | 5/2008 | Volpi et al. | |
| 2008/0114366 | A1 | 5/2008 | Smucker et al. | |
| 2011/0166581 | A1 | 7/2011 | Van Der Merwe et al. | |
| 2012/0059382 | A1 | 3/2012 | Paulos | |
| 2013/0030443 | A1 * | 1/2013 | Wright | A61B 17/158 606/96 |
| 2013/0211410 | A1 | 8/2013 | Landes et al. | |
| 2014/0039552 | A1 | 2/2014 | Pilgeram | |
| 2015/0150570 | A1 | 6/2015 | Okuno et al. | |
| 2016/0135822 | A1 | 5/2016 | Lizardi et al. | |
| 2016/0374694 | A1 * | 12/2016 | Haberman | A61B 90/06 606/80 |
| 2017/0020538 | A1 | 1/2017 | Wong et al. | |
| 2017/0042598 | A1 | 2/2017 | Santrock et al. | |
| 2017/0281202 | A1 * | 10/2017 | Hampp | A61B 34/20 |
| 2018/0110542 | A1 | 4/2018 | DeVasConCellos | |
| 2018/0280069 | A1 | 10/2018 | Barmes et al. | |
| 2019/0167281 | A1 | 6/2019 | Zilberman et al. | |
| 2021/0378683 | A1 * | 12/2021 | Petteys | A61B 17/158 |
| 2022/0409217 | A1 * | 12/2022 | Berger | A61B 17/1778 |
| 2023/0404598 | A1 * | 12/2023 | Steeven | A61B 17/1767 |
| 2025/0114216 | A1 * | 4/2025 | Snauwaert | A61F 2/461 |

FOREIGN PATENT DOCUMENTS

| | | |
|---|---|---|
| JP | 2002-102236 | 4/2002 |
| JP | 2003-93419 | 4/2003 |
| JP | 2018-525111 | 9/2018 |
| WO | WO 2017/187436 | 7/2021 |
| WO | WO 2022/130392 | 6/2022 |

OTHER PUBLICATIONS

Invitation to Pay Additional Fees Dated Mar. 15, 2022 From the International Searching Authority Re. Application No. PCT/IL2021/051509. (2 Pages).

Notice of Reason(s) for Rejection Dated Apr. 22, 2025 From the Japan Patent Office Re. Application No. 2023-534724 and Its Translation Into English. (23 Pages).

International Preliminary Report on Patentability Dated Jun. 29, 2023 From the International Bureau of WIPO Re. Application No. PCT/IL2021/051509 (14 Pages).

Supplementary European Search Report and the European Search Opinion Dated Sep. 19, 2024 From the European Patent Office Re. Application No. 21905998.7. (9 Pages).

Office Action Dated Nov. 3, 2025 From the Israel Patent Office Re. Application No. 303898. (4 Pages).

Notice of Reason(s) for Rejection Dated Nov. 25, 2025 From the Japan Patent Office Re. Application No. 2023-534724 and Its Translation Into English. (22 Pages).

\* cited by examiner

502 — DETERMINE PATTERN OF HOLES TO FORM IN A BONE

504 — CONTACT/GRASP OPPOSITE SIDES OF THE BONE AT MULTIPLE POINTS WITH A SELECTED NUMBER OF CONTACT POINTS

506 — DRILL HOLES IN THE BONE IN THE PATTERN DETERMINED PREVIOUSLY

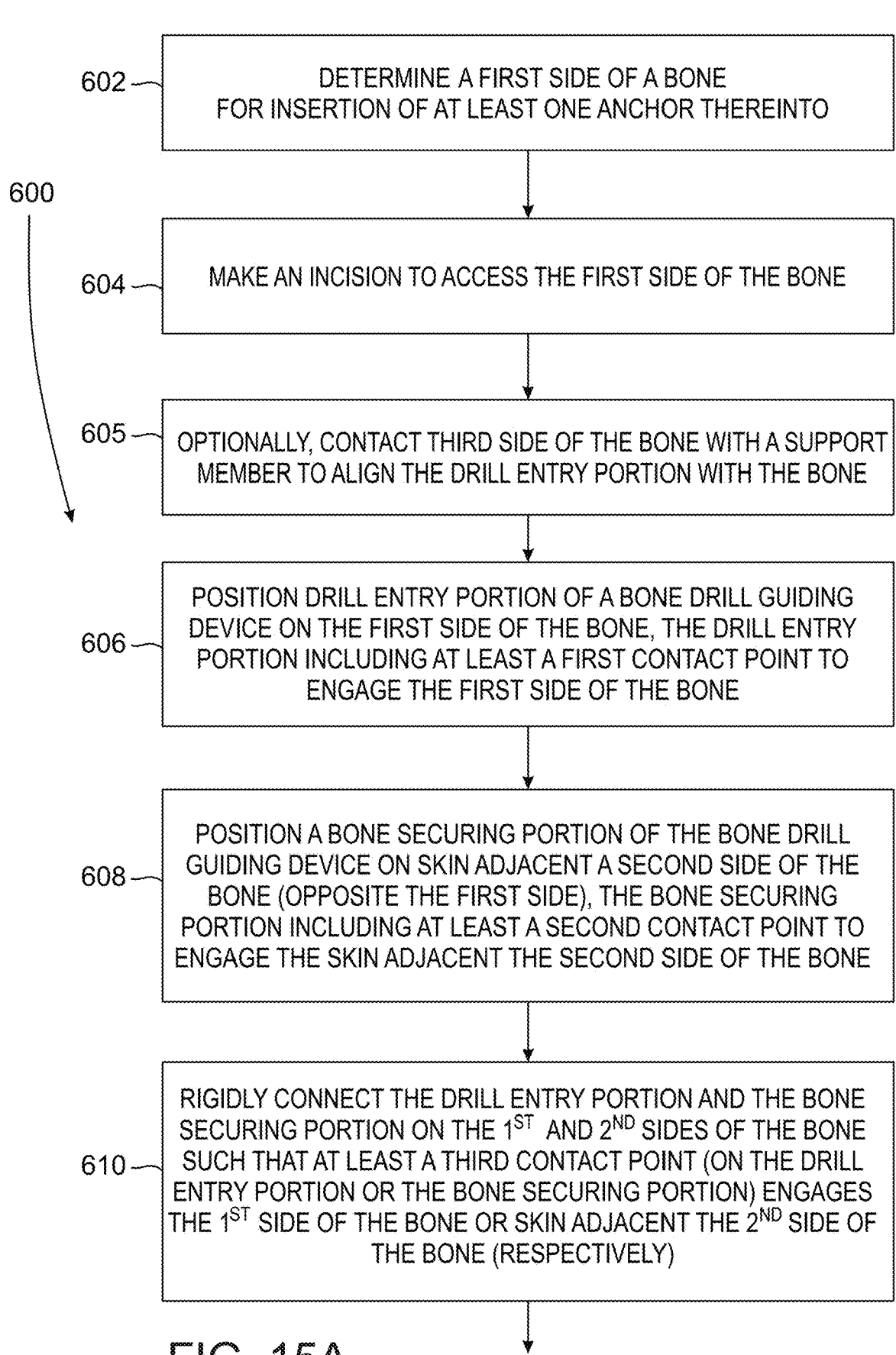

602 — DETERMINE A FIRST SIDE OF A BONE
FOR INSERTION OF AT LEAST ONE ANCHOR THEREINTO

600

604 — MAKE AN INCISION TO ACCESS THE FIRST SIDE OF THE BONE

605 — OPTIONALLY, CONTACT THIRD SIDE OF THE BONE WITH A SUPPORT
MEMBER TO ALIGN THE DRILL ENTRY PORTION WITH THE BONE

606 — POSITION DRILL ENTRY PORTION OF A BONE DRILL GUIDING
DEVICE ON THE FIRST SIDE OF THE BONE, THE DRILL ENTRY
PORTION INCLUDING AT LEAST A FIRST CONTACT POINT TO
ENGAGE THE FIRST SIDE OF THE BONE

608 — POSITION A BONE SECURING PORTION OF THE BONE DRILL
GUIDING DEVICE ON SKIN ADJACENT A SECOND SIDE OF THE
BONE (OPPOSITE THE FIRST SIDE), THE BONE SECURING
PORTION INCLUDING AT LEAST A SECOND CONTACT POINT TO
ENGAGE THE SKIN ADJACENT THE SECOND SIDE OF THE BONE

610 — RIGIDLY CONNECT THE DRILL ENTRY PORTION AND THE BONE
SECURING PORTION ON THE 1$^{ST}$ AND 2$^{ND}$ SIDES OF THE BONE
SUCH THAT AT LEAST A THIRD CONTACT POINT (ON THE DRILL
ENTRY PORTION OR THE BONE SECURING PORTION) ENGAGES
THE 1$^{ST}$ SIDE OF THE BONE OR SKIN ADJACENT THE 2$^{ND}$ SIDE OF
THE BONE (RESPECTIVELY)

FIG. 15A

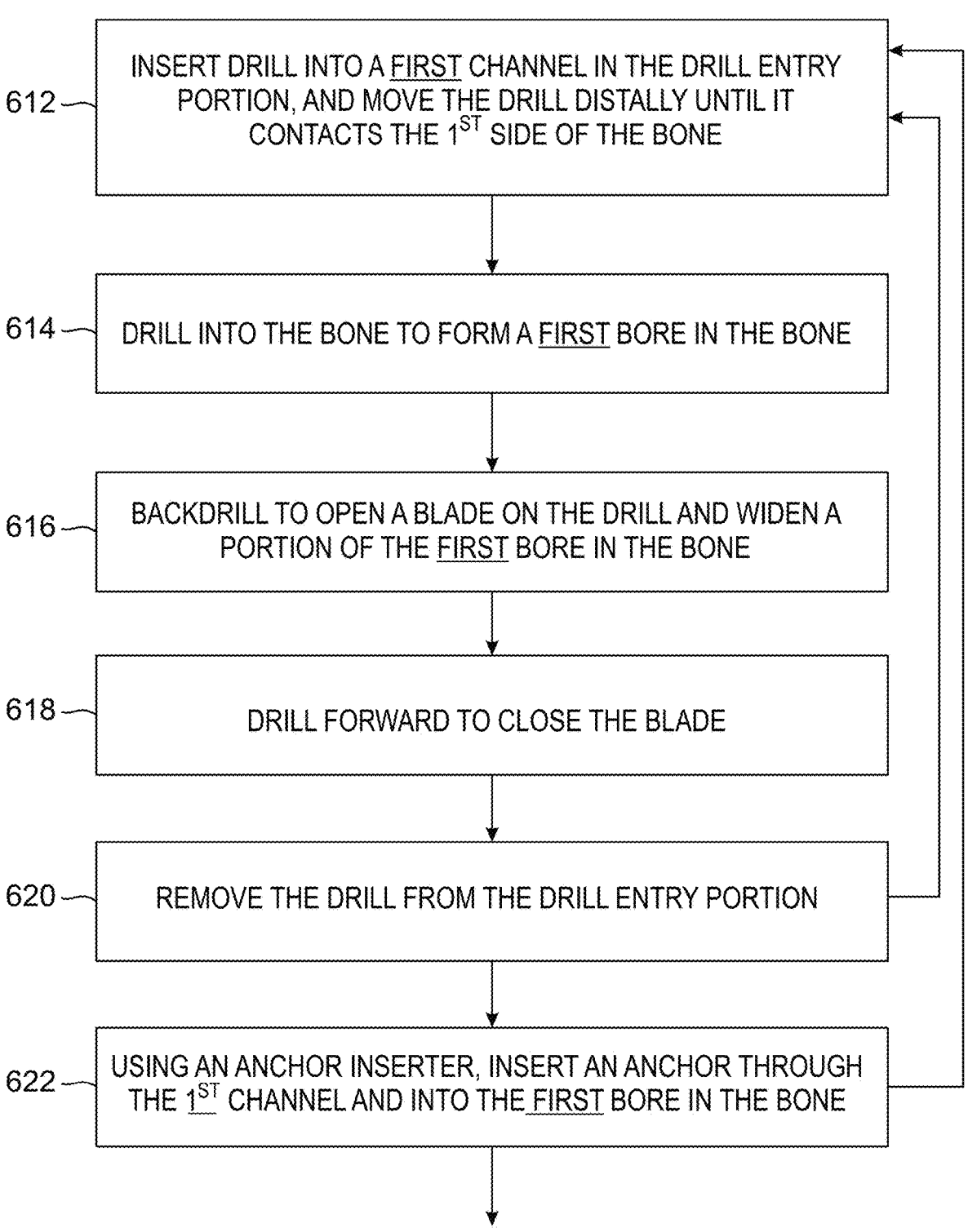

612 — INSERT DRILL INTO A <u>FIRST</u> CHANNEL IN THE DRILL ENTRY PORTION, AND MOVE THE DRILL DISTALLY UNTIL IT CONTACTS THE 1<sup>ST</sup> SIDE OF THE BONE 614 — DRILL INTO THE BONE TO FORM A <u>FIRST</u> BORE IN THE BONE 616 — BACKDRILL TO OPEN A BLADE ON THE DRILL AND WIDEN A PORTION OF THE <u>FIRST</u> BORE IN THE BONE

618 — DRILL FORWARD TO CLOSE THE BLADE

620 — REMOVE THE DRILL FROM THE DRILL ENTRY PORTION

622 — USING AN ANCHOR INSERTER, INSERT AN ANCHOR THROUGH THE 1<sup>ST</sup> CHANNEL AND INTO THE <u>FIRST</u> BORE IN THE BONE

FIG. 15B

624 — RELEASE CONNECTION BETWEEN THE DRILL ENTRY PORTION AND THE BONE SECURING PORTION AND REMOVE THE DEVICE FROM THE SURGICAL SITE

626 — PULL SUTURE(S) ON ANCHOR(S) TO FIX ANCHOR(S) IN PLACE IN THE BORE(S) ON THE BONE

628 — ATTACH THE ANCHOR(S) TO A TENDON AND ATTACH THE TENDON TO ANOTHER BONE

630 — CLOSE THE INCISION

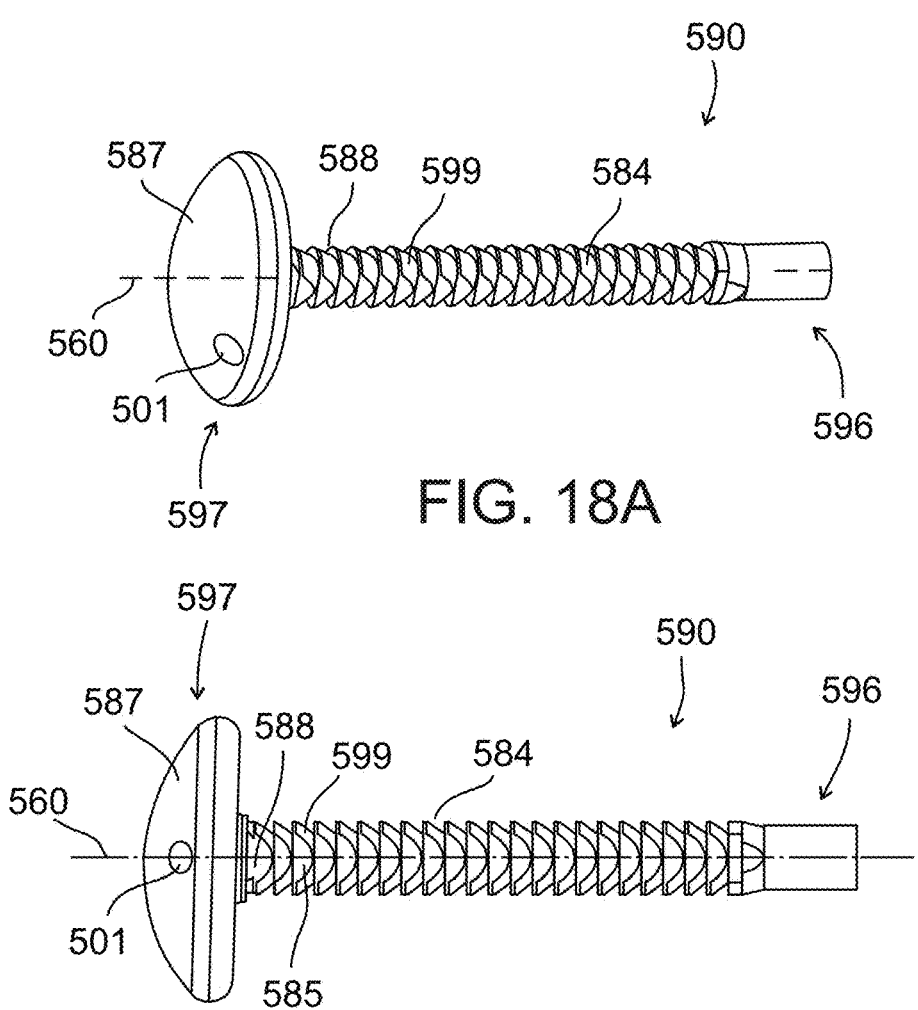
FIG. 18A
FIG. 18B
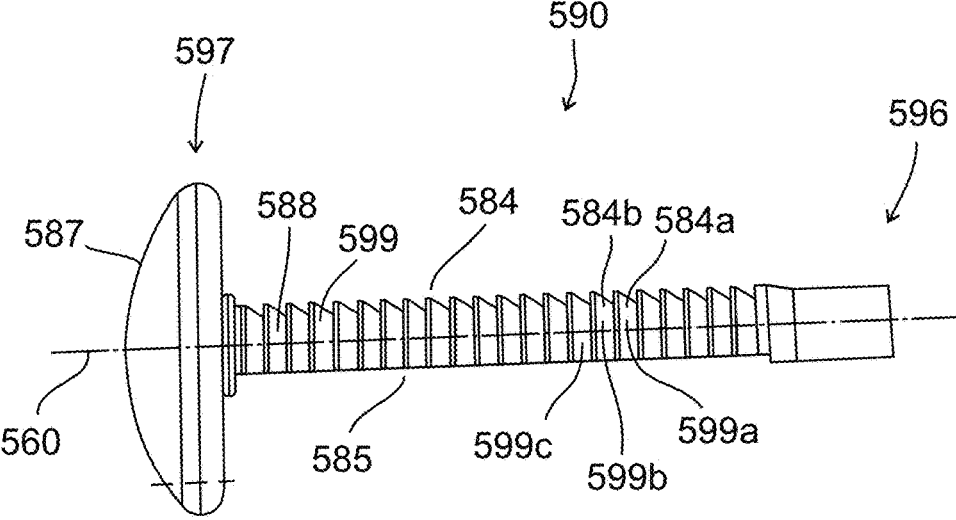
FIG. 18C

OFFSET GUIDING DEVICE AND METHOD OF USE THEREOF

RELATED APPLICATION/S

This application is a National Phase of PCT Patent Application No. PCT/IL2021/051509 having International filing date of Dec. 20, 2021, which claims the benefit of priority under 35 USC § 119(e) of U.S. Provisional Patent Application No. 63/128, 117 filed on Dec. 20, 2020. The contents of the above applications are all incorporated by reference as if fully set forth herein in their entirety.

FIELD AND BACKGROUND OF THE INVENTION

The present invention, in some embodiments thereof, relates to a guiding device and, more particularly, but not exclusively, to an offset drill guiding device and method of use thereof.

It is known that during various arthroscopic procedures drilling into a bone is required. For example, during Anterior Cruciate Ligament Reconstruction (ACL Reconstruction), anteromedial drilling of a femoral tunnel is required.

During this procedure, any of a number of different fixation techniques may be employed in order to drill a bore having predetermined dimensions through the femur bone. It is useful to provide accurate determination of drilling entry point and fixation of exit point during the ACL reconstruction procedure.

While known devices may be useful to facilitate fixation of an elongate bone such as a femur and to facilitate guiding of a drill as it drills through the bone, such devices may not be suitable for smaller bones or bones which are not elongate such as, for example, a patella (kneecap). It would be useful to provide a fixation device and technique suitable for surgical procedures that are to be performed on bones having various shapes and sizes such as, for example, other than elongate.

It is known that during various arthroscopic procedures different fixation techniques are employed in order to drill a bore having predetermined dimensions through a bone. It is useful to provide accurate determination of drilling entry point and fixation of exit point during the procedure.

Background art includes U.S. Pat. Nos. 5,330,468; 5,643,273; and 9,198,676; U.S. Patent Application Publications Nos. 2015/0150570; 2012/0059382; 2014/0039552; 2011/0166581; 2008/0103506; and 2019/0167281; and WO 2017/187436.

SUMMARY OF THE INVENTION

According to an aspect of some embodiments of the present invention there is provided a bone drill guiding device, comprising: a drill entry portion including a first contact point for engaging a first side of a bone, wherein the drill entry portion includes at least one bore sized to receive a bone drill therethrough; a bone securing portion including a second contact point for engaging a second side of the bone, the second side of the bone opposite the first side of the bone; wherein the device includes a third contact point on one of the drill entry portion and the bone securing portion; and a coupling to selectably rigidly connect the drill entry portion and the bone securing portion for positioning the drill entry portion and the bone securing portion on opposite sides of the bone.

According to some embodiments of the invention, the third contact point is on one of the drill entry portion and the bone securing portion.

According to some embodiments of the invention, the drill entry portion includes the first contact point for one of: directly engaging the first side of the bone; and engaging the first side of the bone through intermediate tissue.

According to some embodiments of the invention, the bone securing portion includes the second contact point for one of: directly engaging the second side of the bone; and engaging the second side of the bone through intermediate tissue.

According to some embodiments of the invention, the device includes an adjustable fixation element, wherein the second contact point is defined by a proximal point of the adjustable fixation element, the fixation element movable axially and proximally relative to the bone securing portion to engage the second side of the bone, the fixation element movable axially and distally relative to the bone securing portion to release the second side of the bone from the bone securing portion.

According to some embodiments of the invention, the adjustable fixation element includes a screw thread rotatable in a first direction to move the fixation element proximally relative to the bone securing portion and rotatable in a second direction opposite to the first direction to move the fixation element distally relative to the bone securing portion.

According to some embodiments of the invention, the adjustable fixation element includes a fixation tip, and the adjustable fixation element includes a lock for retaining the fixation tip at an extended or retracted position relative to the bone securing portion.

According to some embodiments of the invention, the device has a longitudinal axis and the drill entry portion includes a single channel having a longitudinal axis which is coaxial with the device longitudinal axis, the adjustable fixation element having a longitudinal axis which is also coaxial with the channel longitudinal axis.

According to some embodiments of the invention, the device has a longitudinal axis and the drill entry portion comprises a plurality of channels, each channel sized to receive the bone drill therethrough and each channel having a longitudinal axis at a preselected orientation relative to the device longitudinal axis.

According to some embodiments of the invention, each channel has a longitudinal axis parallel to the device longitudinal axis.

According to some embodiments of the invention, each of the channels has a longitudinal axis, the longitudinal axes of the channels being parallel to one another.

According to some embodiments of the invention, the drill entry portion includes first and second channels.

According to some embodiments of the invention, the longitudinal axes of the channels are spaced apart by about 5 mm.

According to some embodiments of the invention, the drill entry portion includes first and second distally extending contact portions adjacent the first and second channels, respectively, the first and second distally extending contact portions defining the first and third contact points, respectively.

According to some embodiments of the invention, the device further includes a third distally extending contact portion that extends out of the drill entry portion, wherein the first, second, and third distally extending contact portions define an isosceles triangle with a base at the first and second distal contact portions.

According to some embodiments of the invention, the third distal contact portion is configured to contact a third side of the bone, the third side of the bone between the first and second sides.

According to some embodiments of the invention, the coupling includes a stabilizing portion configured to contact skin adjacent an upper surface of the bone between the drill entry portion and the bone securing portion.

According to some embodiments of the invention, the stabilizing portion is configured to be extendible from the coupling to contact the skin adjacent the upper surface of the bone.

According to some embodiments of the invention, at least one of: (a) the bone securing portion includes an open ended portion directed proximally, the open ended portion including a plurality of contact points for contacting the second side of the bone; and (b) the drill entry portion includes an open-ended portion positioned around the at least one bore, the open-ended portion having an open end directed distally, the open end including a plurality of contact points for contacting the first side of the bone; wherein first and second ones of the plurality of contact points include the first contact point and the third contact point; and wherein the first and second ones of the plurality of contact points are farther apart than twice the diameter of a the bore.

According to some embodiments of the invention, the drill entry portion includes a gripping portion, the gripping portion including the first and third contact points, and wherein the gripping portion includes a concave surface including the first and third contact points.

According to some embodiments of the invention, the bone securing portion has a proximal end, the bone securing portion proximal end including the third contact point.

According to some embodiments of the invention, the bone securing portion proximal end includes two fixation tips, wherein the second and third contact point are at the most proximal portions of the fixation tips.

According to some embodiments of the invention, the drill entry portion includes a fourth contact point to engage the first side of the bone.

According to some embodiments of the invention, the first, second, third, and fourth contact points are disposed in a single plane and define a quadrilateral with at least one pair of parallel sides, between the first and fourth contact points, and between the second and third contact points, respectively.

According to some embodiments of the invention, the coupling includes an arcuate section extending between the drill entry portion and the bone securing portion.

According to some embodiments of the invention, the coupling is a permanent connection between the drill entry portion and the bone securing portion.

According to some embodiments of the invention, the drill entry portion includes a distal end and the bone securing portion includes a proximal end, and the bone drill guiding device includes an indicator configured to indicate a spatial relationship between the drill entry portion distal end and the bone securing portion proximal end.

According to some embodiments of the invention, the drill entry portion includes a marker configured to provide alignment between the device and the bone.

According to some embodiments of the invention, the marker is configured to provide a tactile marking in the bone.

According to some embodiments of the invention, the marker is configured as one of a dot, a circle, a cross, and an X.

According to some embodiments of the invention, the device further includes a handle connectable to the drill entry portion at a selected one of a plurality of sides of the drill entry portion.

According to some embodiments of the invention, there is provided a kit including the bone drill guiding device, the kit further including: a drill sized to be received in the at least one bore; an anchor sized to be received in the at least one bore; and an anchor inserter.

According to an aspect of some embodiments of the present invention there is provided a method of drilling a bore in bone comprising: positioning a drill entry portion of a bone drill guiding device on a first side of a bone, wherein the drill entry portion includes at least one bore sized to receive a bone drill therethrough; positioning a bone securing portion on a second side of the bone, the second side of the bone opposite the first side of the bone; moving the drill entry portion and the bone securing portion toward each other until at least a first contact point of the drill entry portion engages the first side of the bone and at least a second contact point of the bone securing portion engages the second side of the bone, wherein the drill entry portion and the bone securing portion collectively contact the bone at at least three points including the first and second contact points; inserting a drill into a proximal end portion of the drill entry portion until it contacts the bone; and drilling a bore a preselected distance in the bone with the drill.

According to some embodiments of the invention, the engaging includes one of: (a) the drill entry portion contacting the bone at at least two points on the first side of the bone and the bone securing portion contacting the bone at at least one point on the second side of the bone; and (b) the drill entry portion contacting the bone at at least one point on the first side of the bone and the bone securing portion contacting the bone at at least two points on the second side of the bone.

According to some embodiments of the invention, the moving includes: axially sliding the drill entry portion and the bone securing portion towards each other.

According to some embodiments of the invention, the bone drill guiding device has a longitudinal axis and the moving is performed along an axis parallel to the device longitudinal axis.

According to some embodiments of the invention, the drill entry portion includes a handle that is selectively connectable to the drill entry portion at one of multiple locations radially spaced around the bore, the method further including, before the drilling: selecting one of the multiple locations at which to connect the handle; and connecting the handle to the drill entry portion at the selected location.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a schematic illustration of a top view of a device including at least three contact points, in accordance with some embodiments of the invention, the device shown from the top, with portions removed to illustrate the relative locations of the contact points;

FIG. 1B is a schematic illustration of a side view of the device shown in FIG. 1A, takin the direction of arrows 1B-1B therein, in accordance with some embodiments of the invention;

FIG. 1C is a schematic illustration of a first alternative embodiment of the device shown in FIG. 1B, in accordance with some embodiments of the invention;

FIG. 1D is a schematic illustration of a second alternative embodiment of the device shown in FIG. 1B, in accordance with some embodiments of the invention;

FIGS. 15A-C show a flowchart illustrating detailed actions performed by a surgeon during a procedure including forming at least one bore in a bone, in accordance with embodiments of the invention;

FIGS. 18A and 18B-C are respective perspective and side views of a fixation element in accordance with the fourth embodiment of the present invention.

DESCRIPTION OF SPECIFIC EMBODIMENTS OF THE INVENTION

Figure 2A:
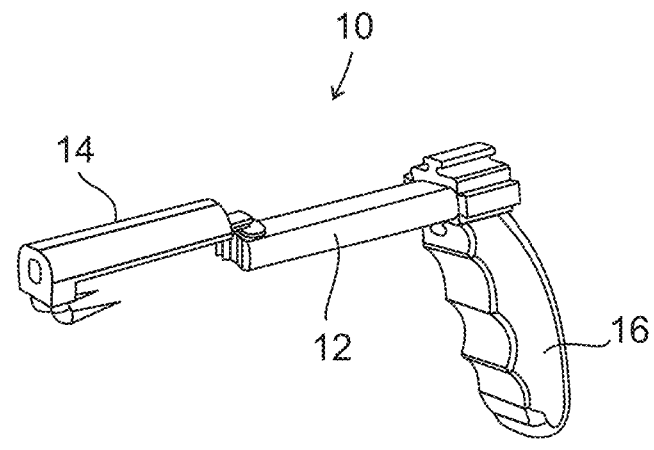
FIG. 2A is a perspective view of a bone drill guiding device according to a first embodiment of the invention.

The present invention, in some embodiments thereof, relates to a guiding device and, more particularly, but not exclusively, to an offset drill guiding device and method of use thereof.

In some embodiments, the device may be adapted for use in procedures including drilling into a bone, for example in order to provide lateral control for drilling a bore in the bone for insertion thereinto of at least one anchor or for other procedures. Such lateral control includes guiding of the drill to a specific entry point on the bone and guiding of the drilling angle, thereby controlling the angle at which the bore is drilled into the bone. In some embodiments, the device may be especially suited for use in procedures including drilling into a bone having a particular size and shape such as, for example, a patella. Some embodiments of the device include portions for stabilizing and/or securing the device relative to a bone and for guiding a drill toward a drill entry point on the bone, in order to drill a bore in the bone at a desired location and angle and to a desired depth within the bone.

An aspect of some embodiments of the present invention relates to the provision of at least three contact points, for example, at least one contact point on a first side of the bone and at least two contact points on a second side of the bone opposite the first side, at which the device may be engaged with or otherwise secured to the bone. The provision of at least three contact points may have a potential advantage in that they may be used to engage and/or grasp a small bone (optionally through skin adjacent the bone) and/or a bone that has curved sides that may be difficult to engage and/or grasp such as, for example, a patella, to prevent inadvertent movement of the bone during a drilling procedure. For example, a patella is a free-floating bone that is not rigidly attached to other structures in the knee, and so it is useful to stabilize it prior to a bone drilling procedure. The device according to the present invention may provide the necessary features for achieving this stabilizing effect.

An aspect of some embodiments of the present invention relates to drilling into a bone at an orientation which is parallel to the plane of a flat bone. This may be useful, especially if the bone is relatively thin and the bore must be drilled into the thin side of the bone, without interfering with the surgeon's flexibility in aligning the device with the drilling site on the bone.

An aspect of some embodiments of the present invention relates to drilling multiple bores in predefined orientations relative to each other in a single plane. For example, in some embodiments of the present invention, multiple bores may be drilled in parallel orientations in a single plane. This may have another potential advantage in that positioning of multiple bores in the bone, where the bores have predefined orientations relative to each other, may be more easily accomplished, relative to such positioning using known devices, thereby reducing the time of a surgical procedure by a few minutes.

An aspect of some embodiments of the invention relates to providing stabilization of a bone which may allow more accurate drilling of at least one bore into the bone. It should be noted that inaccurate drilling into a bone may result in improper angle and/or depth of anchor insertion into the bone which may cause damage to bone and, thereby, to the joint containing the bone. The present invention in some embodiments may also have another potential advantage in that it may allow a bore to be accurately drilled at a selected angle and depth and this may be helpful for insertion of an anchor in the bore at the proper angle and depth.

An aspect of the invention relates to the inclusion of a portion which forms a mark on the bone at a known position relative to a drilled bore. This provides a potential advantage in that it may allow the surgeon to more easily locate the drilled bore after the device has been removed from the surgical site. In some embodiments the mark is formed automatically when the device is engages/is pressed against the bone. In some embodiments the mark is laterally symmetric and/or rotationally symmetric relative to the drilled bore.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figures 1A, 1B, 1C, 1D:
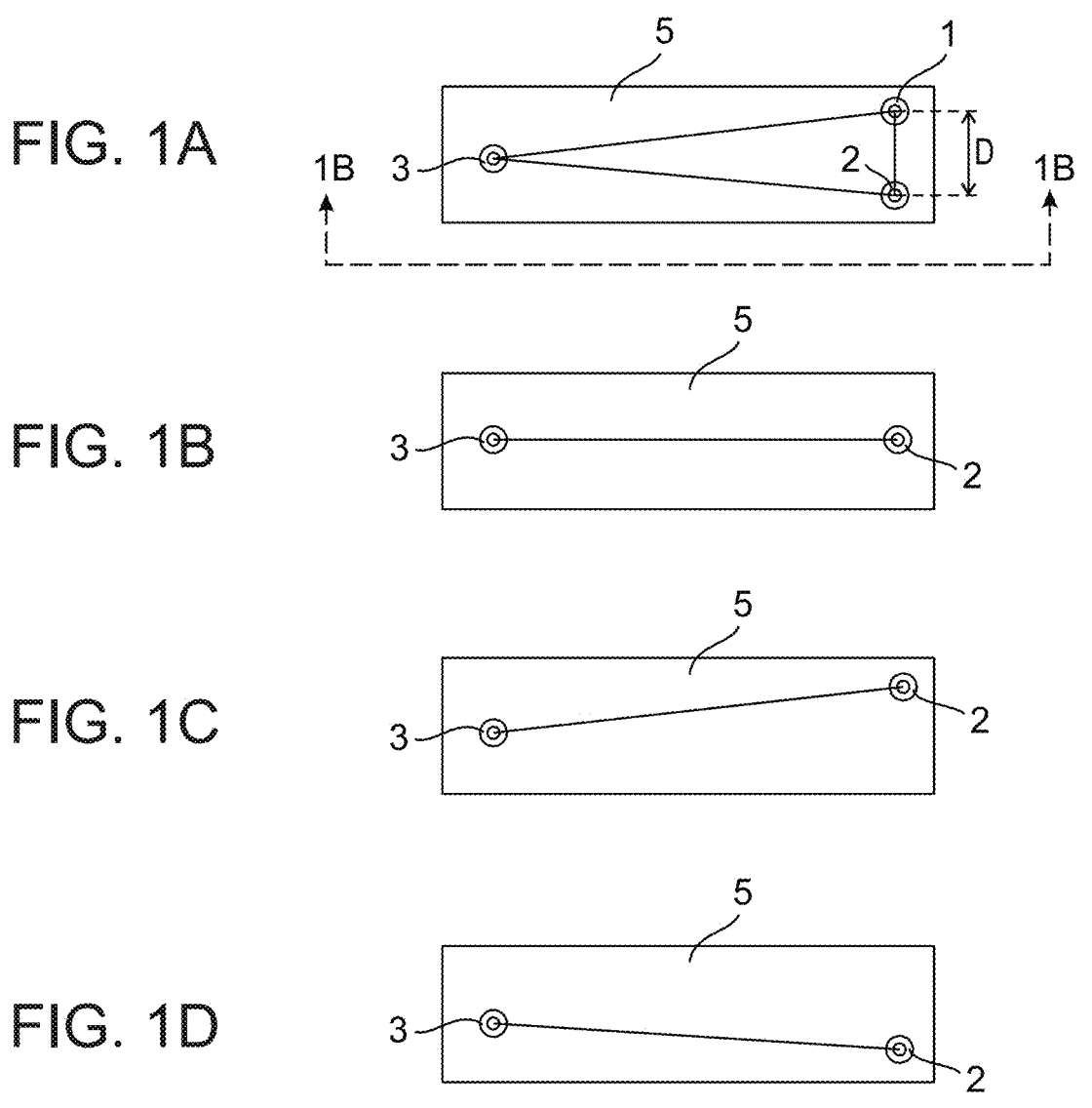

Referring now to the drawings, FIG. 1A is a schematic illustration of a top view of a device 5 including contact points 1, 2, and 3, in accordance with some embodiments of the invention, the device shown from the top, with portions removed to illustrate the relative locations of the contact points.

According to some embodiments, the device may be secured relative to a bone at least at contact points 1, 2, and 3, for example, with at least contact point 1 on a first side of the bone and at least contact points 2 and 3 on a second side of the bone opposite the first side, at which the device may be engaged with or otherwise secured to the bone. Optionally, at least one of the contact points may not directly engage the bone but instead may engage skin adjacent the bone. In some embodiments, a contact point may be a point of contact between the device of the present invention and the bone or skin adjacent the bone and/or may be defined as an area at which a device of the present invention engages with a bone or with skin adjacent the bone. For example, a contact point may be a point at which a channel or an extended portion of the device adjacent a channel, contacts a bone. Alternatively, in some embodiments, a contact point may be associated with a channel, and may be positioned laterally relative to the channel. Examples of contact point positions are discussed in detail hereinbelow. When describing contact or engagement with a bone, this is intended to include, optionally, contact or engagement with skin adjacent a bone.

In the embodiment shown in FIG. 1A, contact points 1, 2, and 3 define an isosceles triangle. Preferably, a distance D between contact points 1 and 2 may be, for example, 5 mm, although any suitable distance may be selected such as, for example, 30 mm, 25 mm, 20 mm, 15 mm, 10 mm, 9 mm, 8 mm, 7 mm, 6 mm, 4 mm, 3 mm, 2 mm, 1 mm, or any larger or smaller distance, as desired. The distance between contact points 1 and 2 may also depend on the particular embodiment of the device or on the bone which is to be engaged, as discussed further herein. For example, contact points defining an isosceles triangle may have a potential benefit in that it may be more suitable for engaging a bone that has a generally symmetric configuration, relative to a longitudinal axis of the device.

Optionally, contact points 1, 2, and 3 may all be in a single horizontal plane, as shown in FIG. 1B. Alternatively, as shown in FIGS. 1C-D, contact point 1 (not shown in these views) and contact point 2 may be in the same horizontal plane, while contact point 3 may be at a relatively lower orientation (FIG. 1C) or at a relatively higher orientation (FIG. 1D). This may have a potential benefit in that it may be more suitable, for example, for engaging a relatively thin bone such as a patella.

Optionally, at least one of the three contact points may be at a position at least partly on an underside of the bone. Optionally, the device may include four contact points which define a quadrilateral with at least one pair of parallel sides.

In embodiments, the device may be constructed such that it is minimally invasive, i.e., only a minor incision is made in skin and other tissue on a first side of the bone, in order to allow at least one contact point of a first portion of the device to engage the bone on the first side of the bone. Skin on a second side of the bone, opposite the first side of the bone, may be engaged by a second portion of the device. This feature may provide a potential benefit of minimizing trauma to the area of the bone and reducing recovery time for the patient. With reference to FIGS. 2A-D there is shown a perspective view of a bone drill guiding device 10 according to a first embodiment of the invention. The device may be fabricated of any suitable material such as, for example plastic and metal, the plastic optionally being disposable. Preferably, the device is fabricated mostly or optionally entirely of plastic materials such as, for example polycarbonate, nylon, ABS, etc.

Device 10 includes a drill entry portion 12, for engaging a first side of bone and via which a drill may be guided relative to the first side of a bone; and a bone securing portion 14, for engaging a second side of the bone. With additional reference to FIGS. 3A-5C, the drill entry portion 12 has an elongate body 20 having a longitudinal axis 22, the body 20 including at least one channel 24 extending therethrough, from a proximal end 28 of the body 20 to a distal end 26 of the body 20. Each channel 24 has a bore 30 extending therethrough. Each channel 24 is sized and shaped to receive a bone drill therethrough, which will be discussed further hereinbelow.

In the embodiment shown, the drill entry portion 12 may be provided with two channels 24 which are parallel to axis 22. The distance between the center points 32 (FIG. 3C) of the bores 30 may be for example, 5 mm, as discussed above with regard to FIG. 1A. However, depending on the procedure to be performed, and the number of bores to be drilled and their relative positions, any number of channels may optionally be provided, where the channels are arranged at any preselected orientation relative to each other, the bore center points spaced apart any selected distance, and the channels positioned in the body in any selected configuration. For example, in a procedure in which it is desired to insert four anchors into a bone at positions defining a square shape, a bone drill guiding device may include four parallel channels, the centers of bores of which are configured in a square.

Further, it may be noted that, optionally, the distance between center points 32 of bores 30 in body 20 may be any selected distance, the selected distance dependent at least in part by the diameter of the bores to be drilled. For example, a device in accordance with some embodiments of the present invention may be utilized in a procedure for drilling two parallel bores in a bone, each of the parallel drilled bores having a diameter of, for example, from 0.1-10 mm. For example, a pair of parallel bores, each having a diameter of 10 mm, may be drilled in a bone using the device accordance with some embodiments of the present invention, where the distance between the center points 32 of the bores 30 in body 20 may be, for example, 15 mm.

In the embodiment shown, channels 24 resemble cannulas, with a proximal end 38 of each channel 24 optionally extending past the body proximal end 28. However, if desired, the proximal end of the channels may, alternatively, not extend past the body proximal end 28 but, rather, be flush with the body proximal end 28. This may provide a potential benefit in that the portion of the body that engages the bone may have a wider surface area, thereby providing a more secure grip on the bone.

Figures 3A, 3B:
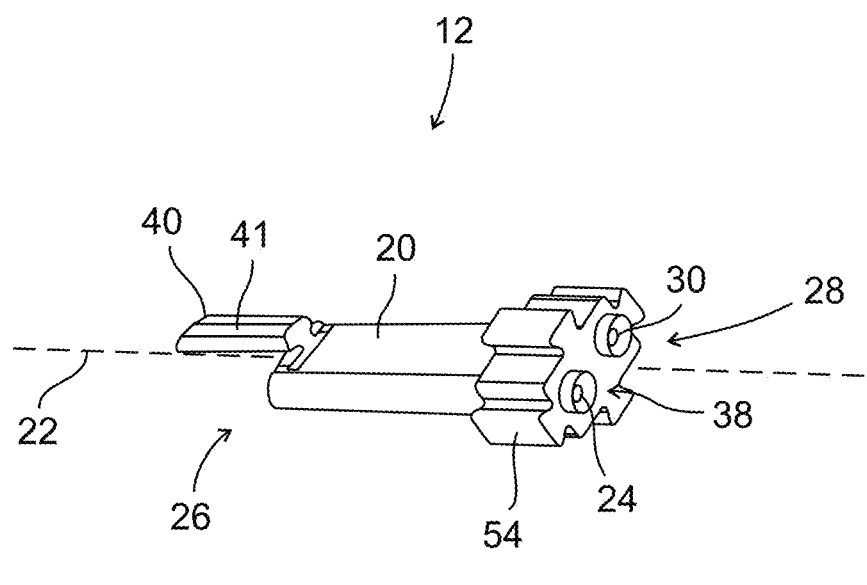
FIGS. 3A and 3B are respective perspective and top views of a guide portion of the device of FIG. 2D, according to the first embodiment of the invention.
Figure 3C:
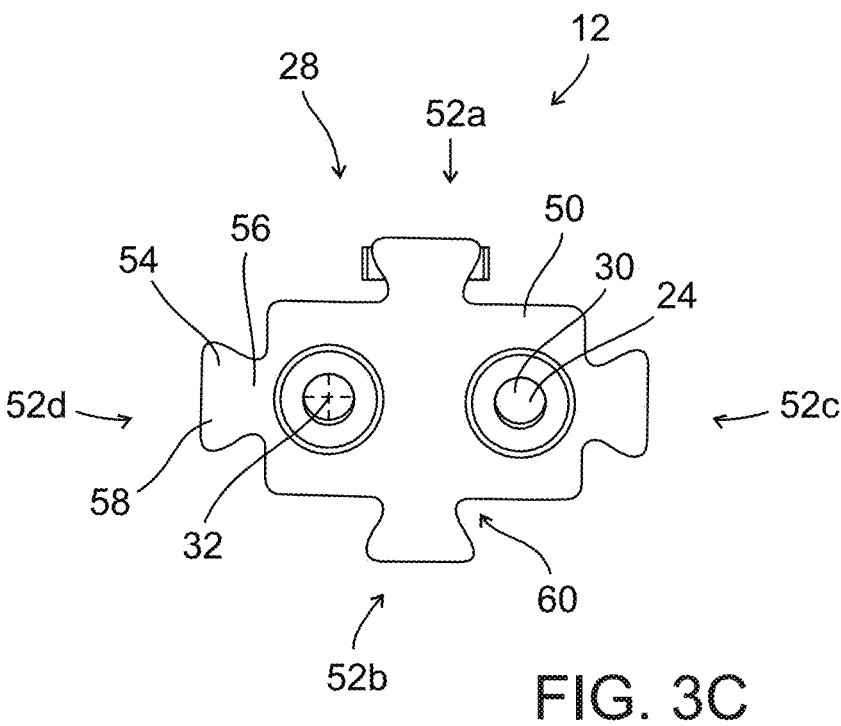
FIG. 3C is a back view of the guide portion shown in FIG. 2D, taken in the direction of arrows 3C-3C therein, according to the first embodiment of the invention.
Figure 3D:
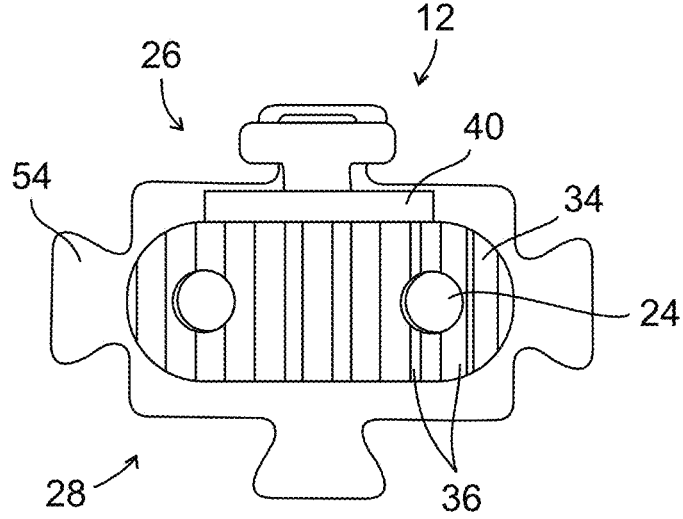
FIG. 3D is a front view of a guide portion shown in FIG. 2D, taken in the direction of arrows 3D-3D therein, according to the first embodiment of the invention.

The body distal end 26 may be provided with an optional gripping surface 34, seen most clearly in FIG. 3D, suitable for contacting and engaging a first side of a bone and preventing the body 20 from moving relative to the bone. In the embodiment shown, gripping surface 34 may be provided with a plurality of raised portions 36 which may, for example, each have a v-shaped cross-section or any other suitable configuration. Optionally, raised portions 36 may resemble teeth. Alternatively, gripping surface 34 may be provided with any suitable texture for engaging the bone and preventing movement of body 20 relative to the bone. Optionally, gripping surface 34 may be smooth. For example, a more textured gripping surface may have a potential benefit in that it may be more suitable for engaging a bone having a smoother surface.

Figure 2B:
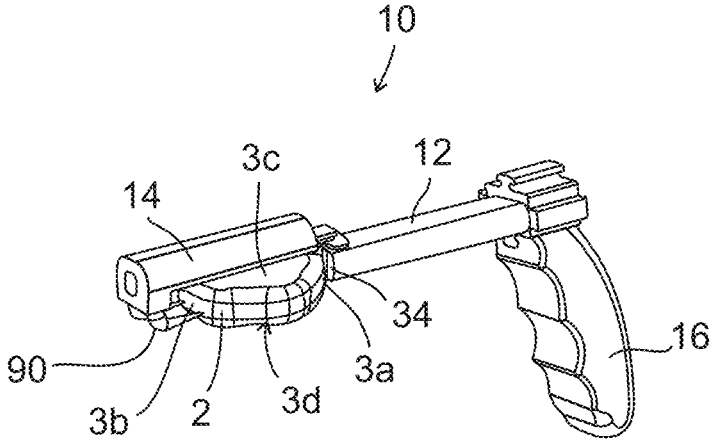
FIG. 2B illustrates the device of FIG. 2A, according to the first embodiment of the invention, the device shown in engagement with a bone.
Figure 2C:
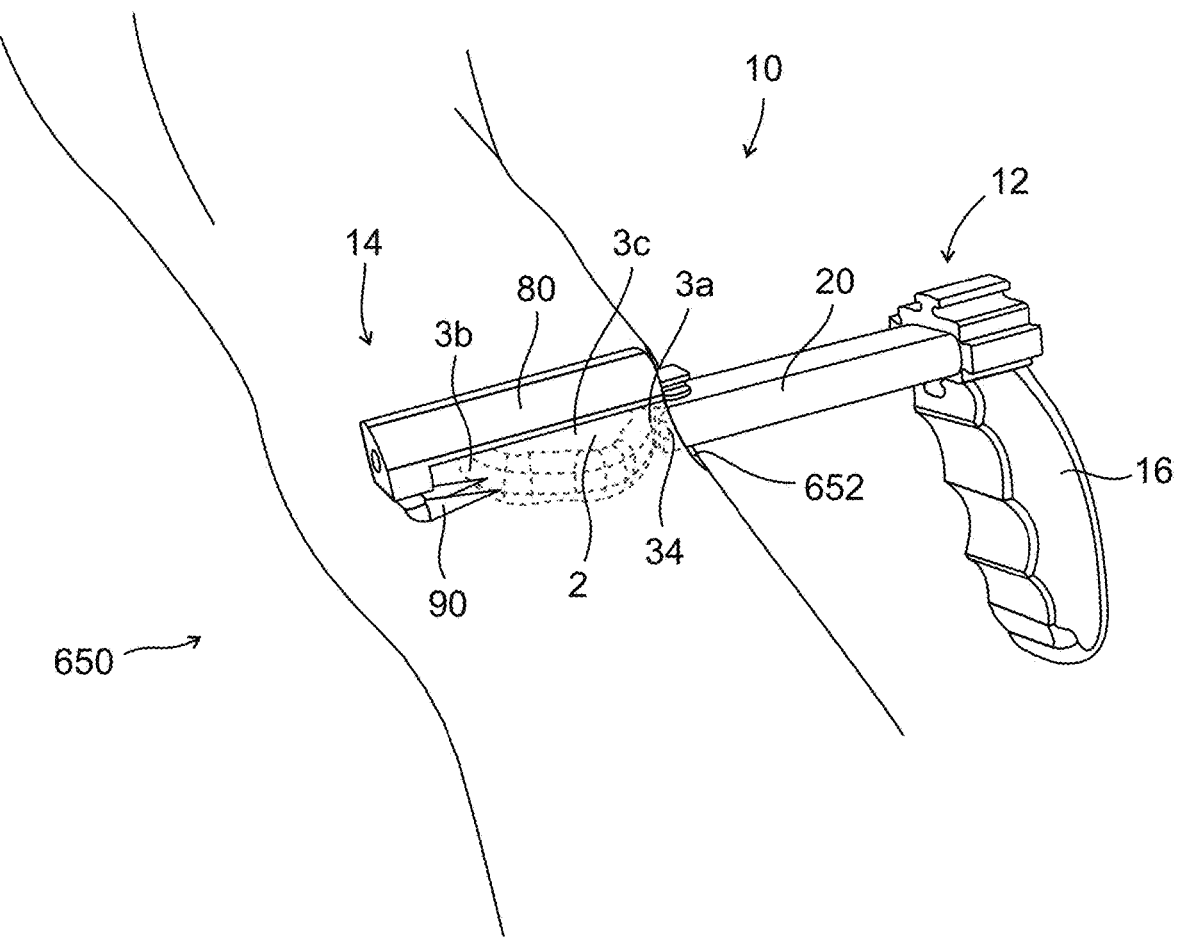
FIG. 2C is an illustration of the bone drill guiding device, according to the first embodiment of the invention, shown engaged with a patella of a patient.
Figure 2D:
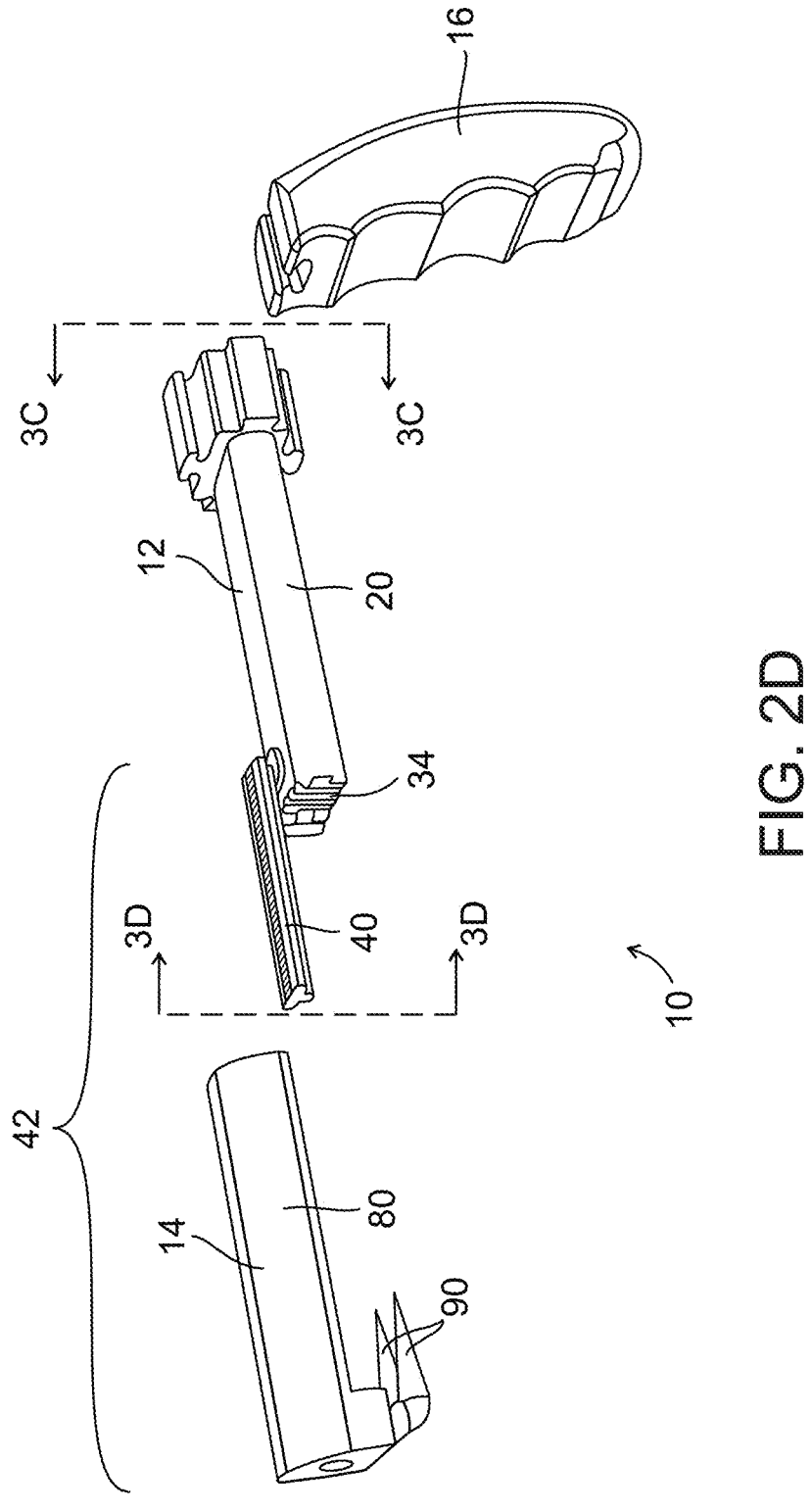
FIG. 2D is an exploded view of the bone drill guiding device of FIG. 2A, according to the first embodiment of the invention.

In the embodiment shown, gripping surface 34 may optionally be a concave surface, as illustrated most clearly in FIG. 2D. A concave gripping surface 34 may facilitate gripping of the bone 2, due to the similarity in configuration between the gripping surface 34 and the first side 3*a* of bone 2.

Optionally, each of channels 24 may protrude out of the body distal end 26 (similar to the way the channel proximal ends 38 extend past the body proximal end 28 as seen in FIG. 3A), such that the protruding channel itself provides at least one point for contacting and engaging the bone. This is discussed further herein.

The drill entry portion may also be provided with a bar 40 for connecting the drill entry portion 12 to the bone securing portion 14, which will be described in more detail below. In the embodiment shown, bar 40 of the drill entry portion defines a first portion of a ratchet mechanism 42 (FIG. 2D) for connecting the drill entry portion to the bone securing portion 14. However, it should be noted that, alternatively, any suitable connection mechanism may be provided for connecting the drill entry portion 12 and the bone securing portion 14 together. For example, a connection mechanism may be particularly shaped so that it may extend around a bone having protruding portions. This may have a potential benefit in that it may be suitable for a device for engaging a bone which might otherwise be difficult to grip.

Optionally, the device 10 may be provided with an indicator (not shown), to indicate a spatial relationship between the distal end 26 of the body 20 of the drill entry portion 12 and the proximal end 82 of the body 80 of the bone securing portion 14. This may facilitate preparation of the device before positioning it relative to the bone 2 (FIGS. 2B-C), and/or securing of the device onto the bone/skin adjacent the bone. Optionally, a portion of at least one of the drill entry portion 12 and the bone securing portion 14 includes the indicator. Optionally, a linear connecting portion of the device such as, for example, bar 40 of ratchet mechanism 42 includes the indicator. Indicators for indicating the spatial relationship between components that are movable relative to each other are known in the art and will not be described further herein.

At the body proximal end 28 of the drill entry portion 12, there may optionally be formed a handle connection portion 50, whereat a handle 16 may be connected to the drill entry portion 12 at one of a number of separate locations positioned radially about the drill entry portion. However, it may be noted that, optionally, the device may not include a handle or may include a handle having a different configuration than that shown in FIG. 2A.

With reference to FIGS. 3A-D there is shown a drill entry portion 12 including body 20 having a bar 40 at its distal end and a handle connection portion 50 at its proximal end.

In the embodiment shown, the handle connection portion 50 includes four connection stations 52*a-d*, one station positioned on each of the respective top, bottom, right side and left side of the body 20, for allowing a handle to be selectably connected at the top, bottom, right side, or left side of the drill entry portion. Optionally, the device may be provided with any other suitable number of connection stations, at any other suitable locations. Optionally, the handle connection stations are radially spaced around the handle connection portion 50.

Each of connection stations 52*a-d* includes an elongate bar 54 which protrudes out of the body proximal end 28 of the drill entry portion 12. Each bar 54 has a base 56 and an outer edge 58. The bar 54 has a trapezoidal-shaped cross-section, such that an elongate v-shaped recess may be provided on either side of the bar 54, adjacent the base 56 thereof.

Figure 5A:
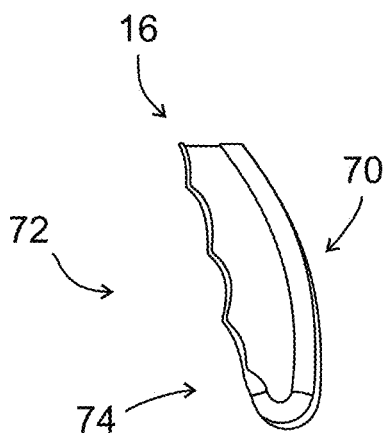
FIGS. 5A, 5B, and 5C are respective side, front, and back views of the handle shown in FIG. 2C, according to the first embodiment of the invention.
Figure 5B:
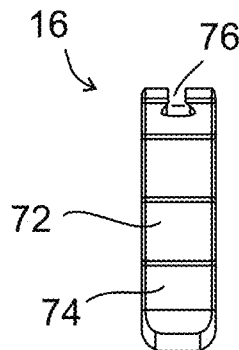
Figure 5C:
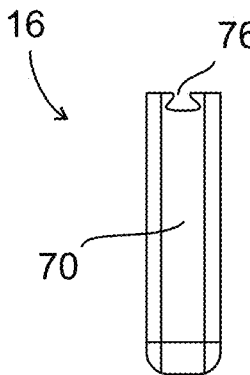

With additional reference to FIGS. 5A-C, there is shown a handle 16 that may be attached to handle connection portion 50 on the drill entry portion 12. Handle 16 includes a back side 70 which may optionally be shaped for being held in a palm of a user of the device. Handle 16 also has a front side optionally having a plurality of curved portions 74 for resting fingers of a user of the device.

The upper end of handle 16 may be provided with an elongate recess 76 having a trapezoidal-shaped cross-section which corresponds in size and shape to the cross-section of bar 54 of the drill entry portion 12. The length of the recess 76 may be substantially the same length as that of the bar 54. This particular structure of the handle 16 and the proximal end 28 of the drill entry portion 12 allows the handle 16 to be easily connected to the drill entry portion 12, at any one of the four connection stations 52a-d.

In order to connect the handle 16 to the drill entry portion 12, a user first decides which of the four connection stations 52a-d may be most suitable for connecting the handle for the particular procedure to be performed. This may depend on whether he wants the handle 16 to be positioned above, below, or to one side of the drill entry portion 12. For example, if connection station 52b is selected, this allows the device to be held with the handle to the side of the drill entry portion 12, as shown in FIG. 2A, and with the handle held below a bone 2, as shown in FIGS. 2B-C. Alternatively if any of the other connection stations 52a, 52c, or 52d is selected, this allows the device to be held with the handle respectively above the drill entry portion 12, to the right side of the drill entry portion, or to the left side of the drill entry portion (these configurations, where handle 16 may be connected at one of connection stations 52a, 52c, and 52d, is not shown in the drawings). Any of these configurations may provide a potential benefit in that it may allow the surgeon to grip the bone from a particular angle that may, for example, allow better visibility of the surgical site and/or may, for example, allow easier access to the surgical site.

In order to connect the handle 16 to the drill entry portion 12, the handle may be held proximal to the drill entry portion, with the handle recess 76 aligned with the bar 54 of the drill entry portion. The bar 56 may be inserted into the recess 76 and slid until it is entirely positioned within the recess. The device 10 may be provided with a friction fit between the bar 54 of the drill entry portion 12 and the recess 76 of the handle 16, for maintaining a connection between the handle 16 and the drill entry portion 12. Alternatively, any other suitable mechanism may be provided for maintaining a connection between the handle 16 and the drill entry portion 12.

It should be noted that handle may be connected below the body 20, and at a position distal to the channel proximal end(s) 38, as seen most clearly in FIG. 2A, so as not to interfere with insertion of a drill or other elements into the channel(s) 24.

Optionally, device 10 may include any other suitable type of handle, connected to the drill entry portion at any suitable location. Optionally, device 10 may include no handle.

Figure 4A:
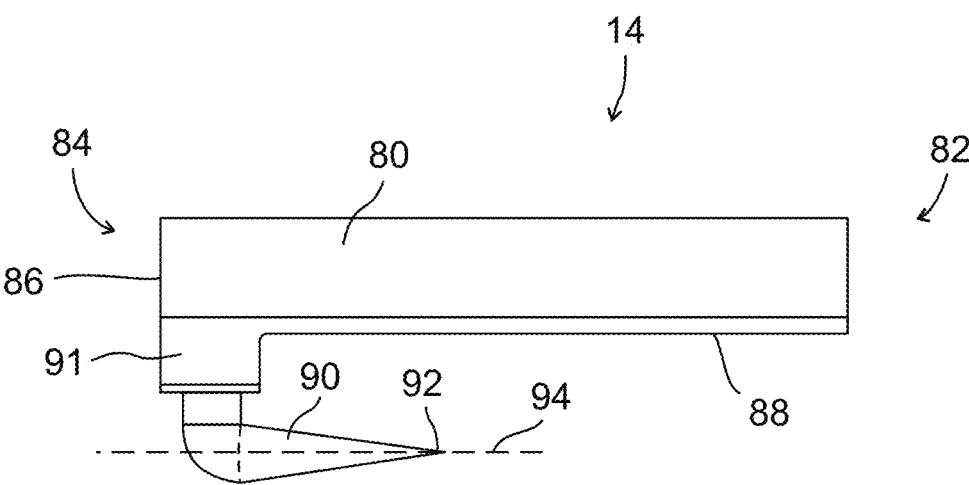
FIGS. 4A and 4B are respective side and perspective views of a fixation portion of a bone drill guiding device according to the first embodiment of the invention.
Figure 4B:
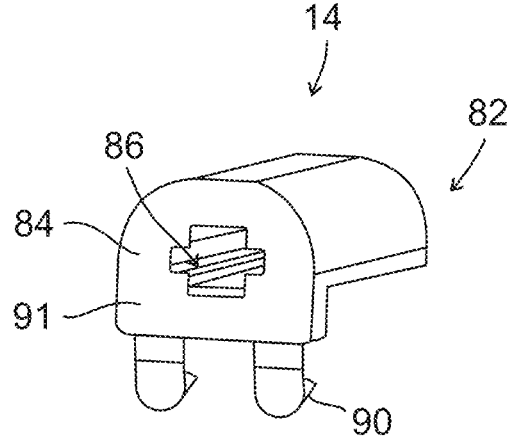
Figure 4C:
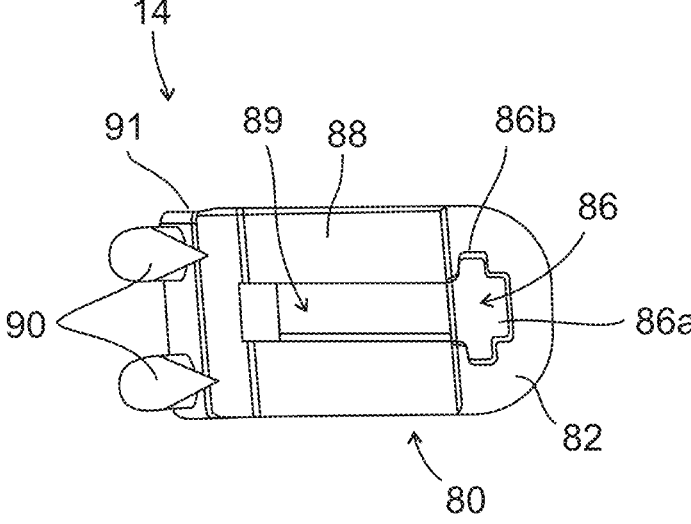
FIG. 4C is a bottom view of the fixation portion shown in FIG. 2D, according to the first embodiment of the invention.

With additional reference to FIGS. 4A-C there is shown bone securing portion 14 according to some embodiments of the invention. Bone securing portion 14 has an elongate body 80 having a proximal end 82, at which body 80 may be connected to drill entry portion 12, and a distal end 84 including a pair of spikes 90, which are discussed further herein.

The body 80 has a passageway 86 extending therethrough, the passageway 86 including a narrower upper portion 86a and a wider lower portion 86b. As shown most clearly in FIG. 4C, body 80 has a lower surface 88 having an opening 89 leading into passageway 86. Alternatively, there may be no opening in lower surface 88. This may provide a potential benefit in that the lower surface 88 may be larger, thereby providing more surface area with which to potentially contact the bone.

Passageway lower portion 86b may be sized and shaped to slidingly receive bar 40 of the drill entry portion 12 (FIG. 3A). The passageway upper portion 86a may be provided with a pawl or teeth (not shown), for engaging teeth 41 on bar 40, the body 80 of bone securing portion 14 thereby defining a second portion of ratchet mechanism 42 (FIG. 2D) for connecting the drill entry portion 12 to the bone securing portion 14. The bar 40 and the passageway lower portion 86b of ratchet mechanism 42 are configured such that bar 40 may be inserted into passageway lower portion 86b, and the drill entry portion 12 and the bone securing portion 14 are movable toward each other by sliding them axially in a path which may be parallel to axis 22, the ratchet mechanism 42 locking them in position relative to each other. As ratchet mechanisms are well known in the art, this will not be described here in detail. Sliding of the drill entry portion 12 and the bone securing portion 14 toward each other so as to contact a bone and engage (and/or skin adjacent a bone) is discussed further herein.

The distal end 84 of body 80 includes a lower portion 91, which extends below body 80, from which depends the pair of spikes 90. Optionally, spikes each depend the same distance below body 80. Spikes 90 extend from lower portion 91 and are directed proximally, below a portion of body 80, such that their tips 92 define the most proximal portions of the spikes 90. Spikes 90 each have a longitudinal axis 94 which may be parallel to axis 22 of drill entry portion when the device is assembled (FIG. 2A). Spikes 90 are each provided with a sharp tip 92 suitable for engaging and gripping a bone, optionally via skin adjacent the bone, as is discussed herein.

Prior to use in a drilling procedure, the handle 16 may be attached to the drill entry portion 12 by sliding bar 54 of the drill entry portion 12 into recess 76 of the handle 16. In the embodiment shown in FIGS. 2A-B, bar 54 which may be on the lower face of drill entry portion 12 (at handle connection station 52b) has been slid into recess 76 of handle 16, such that the handle 16 may be connected to the drill entry portion 12.

In order to rigidly connect the drill entry portion 12 to the bone securing portion 14, the bar 40 of the drill entry portion 12 may be inserted into and slid slightly into passageway lower portion 86b of bone securing portion 14. The device may be positioned on skin adjacent a bone 2, with body lower surface 88 of bone securing portion 14 in contact with skin adjacent an upper surface 3c of the bone 2. The body 80 of bone securing portion 14 may thereby be offset relative to body 20 of drill entry portion 12. Optionally, lower surface 88 of bone securing portion 14 includes a non-skid surface, for example, a textured surface, to securely engage bone upper surface 3c, via skin above bone upper surface 3c, and prevent relative movement between bone securing portion 14 and the bone 2 during a surgical procedure. This is described further in detail herein.

The drill entry portion 12 and bone securing portion 14 are moved toward each other and locked in position, by sliding bar 40 further into passageway lower portion 86b, until the gripping surface 34 of drill entry portion 12 contacts and engages a first side 3a of the bone 2 and the tips 92 of the spikes 90 engage a second side 3b of the bone 2 opposite the first side 3a, via skin adjacent the bone second side 3b. Alternatively, at least one of spikes 90 may contact skin adjacent a lower side 3d of the bone 2, thereby engaging lower side 3d of the bone 2. This may provide a potential benefit in that the bone would then be engaged on three sides, namely sides 3a, 3b, and 3d, which may provide a more secure grip of the bone.

After the surgical procedure has been performed, the drill entry portion 12 and the bone securing portion 14 may be moved axially, away from each other, to disengage the device 10 from the bone (and/or skin adjacent the bone). This feature provides another potential advantage in that the portions of the device may be easily maneuvered to engage the opposite sides of the bone prior to the procedure, optionally engaging skin on at least one side of the bone, and easily maneuvered to disengage from the site of the procedure without causing additional trauma to the surgical site. Optionally, the coupling may be a permanent connection between the first and second portions, and additional portions of the device may be movable toward the bone for engagement with skin adjacent the bone.

Alternatively, instead of body lower surface 88 of bone securing portion 14 being in direct contact with skin adjacent an upper surface 3c of the bone 2, as shown in FIG. 2C, device 10 may be provided with a depending support member (not shown), for example, at a lower surface of bar 40, for contacting skin adjacent a third side 3c of the bone. Such a support member is discussed in detail with regard to FIGS. 6A-9B, regarding the second and third embodiments, and will not be described here. Such a support member may facilitate alignment of the drill entry portion 12 with the first side 3a of the bone 2, as discussed herein with regard to the second and third embodiments (FIGS. 6A-9B).

It should be noted that, in the embodiment shown, the gripping surface 34 provides a plurality of contact points between the drill entry portion 12 and the bone 2. Optionally, at least two contact points provided on gripping surface 34 are provided radially outward relative to channels 24, such that channels 24 are disposed between the two contact points provided on the griping surface. Additionally in the embodiment shown, the pair of spikes 90 provides an additional two contact points between the bone securing portion 14 and skin adjacent the bone 2, at the bone second side 3b.

Optionally, at least one of spikes 90 may at least partially contact skin adjacent the bone lower side 3d, thereby providing at least one additional contact point between device 10 and the bone 2 (or skin adjacent the bone). Optionally, as noted above, each of channels 24 may protrude out of the body distal end 26, whereby each channel 24 provides at least one point for contacting the bone, and spikes 90 each provide at least an additional contact point between the bone securing portion 14 and skin adjacent the bone 2.

Additionally, the lower surface 88 of body 80 of bone securing portion 14 provides further contact with skin adjacent the bone, as discussed above, specifically on skin adjacent the upper side 3c of the bone, which provides additional stability, thereby preventing relative movement between device 10 and the bone 2 during a surgical procedure.

It should be noted, however, that device 10 is specifically designed such that there are a minimum of three contact points between the device and the bone 2 (and/or skin adjacent the bone). The at least three contact points may include at least a single contact point between the drill entry portion 12 and the bone first side 3a, and at least a pair of contact points between the bone securing portion 14 and the bone second side 3b (or skin adjacent the bone second side 3b). Alternatively, the at least three contact points may include at least a pair of contact points between the drill entry portion 12 and the bone first side 3a, and at least a single contact point between the bone securing portion 14 and the bone second side 3b (or skin adjacent the bone second side 3b). Optionally, the first, second, and third contact points are located in a single plane.

Optionally, the drill entry portion 12 includes at least a single contact point, for contacting and engaging the bone first side 3a, the bone securing portion 14 includes at least a pair of contact points for contacting and engaging the bone second side 3b (or skin adjacent the bone second side 3b), and the drill entry portion 12 further includes a fourth contact point, for contacting and engaging the first side 3a of the bone 2. Optionally, the first, second, third, and optional fourth contact points define a quadrilateral with at least one pair of parallel sides, between the first and fourth contact points, and between the second and third contact points, respectively. Provision of at least three contact points, located on at least two opposite sides of the bone 2 (and/or skin adjacent the bone) may provide the device 10 with enhanced stability relative to the bone, allowing the bone to be securely gripped during a surgical procedure such as, for example, drilling into the bone and/or anchor insertion, as discussed herein. Further contact points between the device 10 and the bone (and/or skin adjacent the bone), as noted above, may provide further stability, as discussed herein.

FIGS. 2B-2C illustrate device 10 in engagement with a bone 2 such as a patella, in accordance with some embodiments of the invention such as, for example, during a surgical procedure in which the patella is rigidly engaged. In FIG. 2C the knee 650 and adjacent portions of the patient's leg are shown, with the patella 2 and a portion of device 10 shown in dotted lines to indicate that the patella and that portion of device 10 are beneath the skin of the patient. FIG. 2B shows the identical device 10 and patella 2 as in FIG. 2C, except that in FIG. 2B all parts of the patient's leg except the patella itself have been removed for the sake of clarity.

It may be seen in FIG. 2C that an incision 652 has been made on the side of the patella 2 in which it is desired to drill at least one bore. A portion of device 10 including the gripping surface 34 on body 20 of drill entry portion 12 has been inserted into the incision 652, a sufficient distance such that gripping surface 34 contacts the patella 2. Body 80 of bone securing portion 14 is oriented such that it rests on skin on top of upper surface 3c of the patella. Body 20 of drill entry portion and body 80 of bone securing portion have been moved axially toward each other via ratchet mechanism 42 (FIG. 2D) until spikes 90 engage skin adjacent side 3b of the patella, thereby contacting the patella at multiple contact points as discussed herein.

Figure 6A:
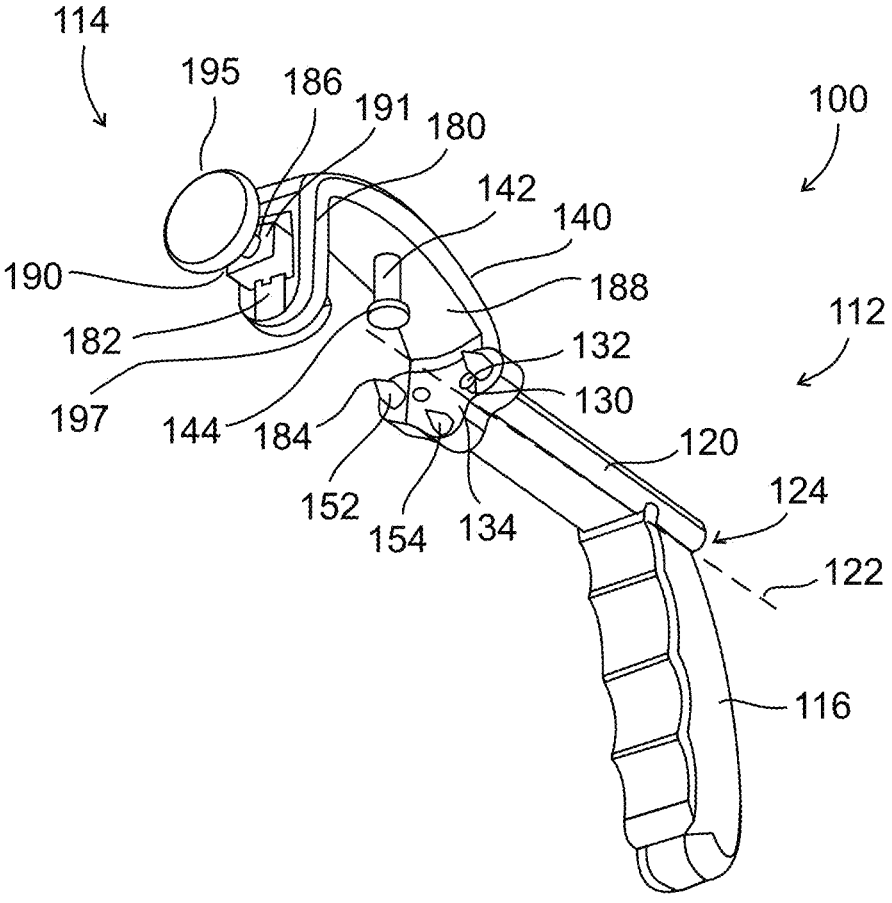
FIGS. 6A and 6B are respective bottom-perspective and side views of a bone drill guiding device according to a second embodiment of the invention.
Figure 6B:
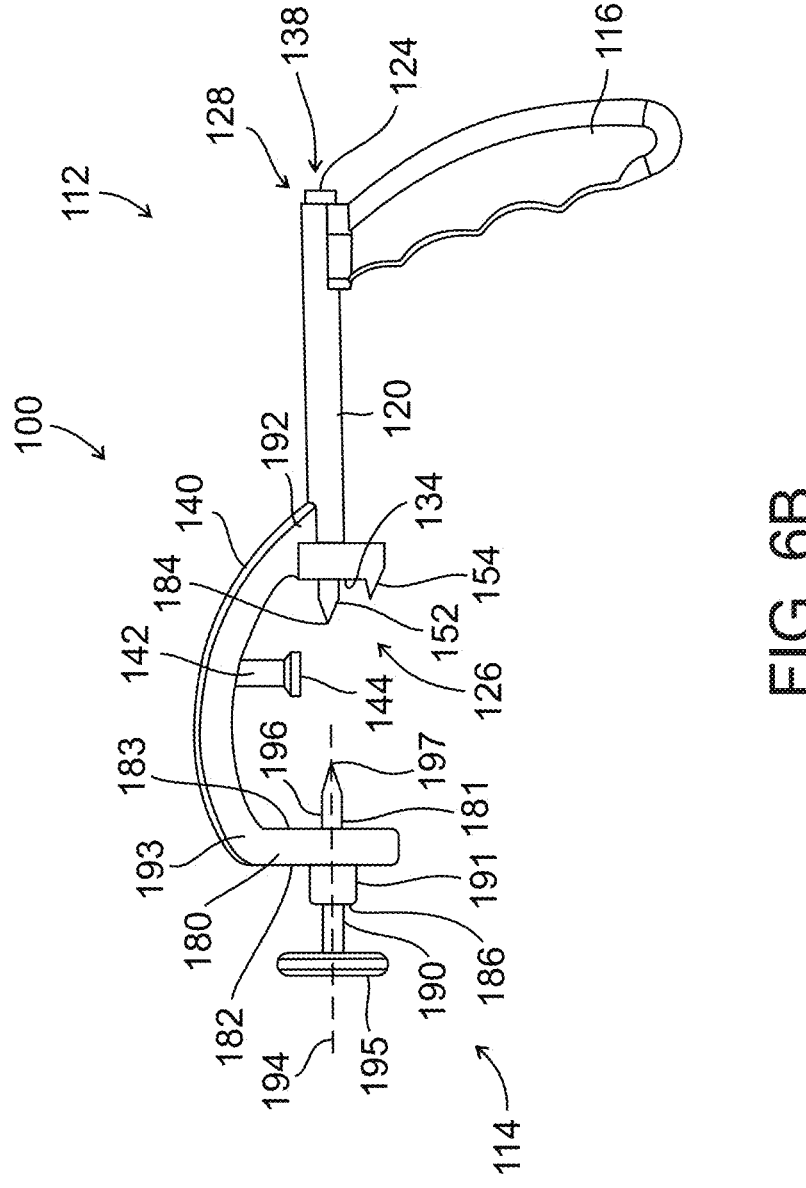

With reference to FIGS. 6A-B there is shown a bone drill guiding device 100 according to a second embodiment of the invention. As some of the components of device 100 are similar in configuration and function as similar components of the first embodiment of the device (FIGS. 2A-5C), they will not be described again in detail.

Device 100 includes a drill entry portion 112, for engaging a first side of bone and via which a drill may be guided relative to the first side of a bone; and a bone securing portion 114, for engaging a second side 3b of the bone 2. Drill entry portion 112 and bone securing portion 114 together provide at least three contact points between the device 100 and the bone 2 and/or skin adjacent the bone.

Drill entry portion 112 has an elongate body 120 having a longitudinal axis 122, body 120 including at least one channel 124 extending therethrough, from a proximal end 128 of the body 120 to a distal end 126 of the body 120. Each channel 124 has a bore 130 extending therethrough. Each channel 124 may be sized to receive a bone drill therethrough, which is discussed further herein.

In the embodiment shown, the drill entry portion 112 may be provided with two channels 124 which are parallel to axis 122. The distance between the center points 132 (FIG. 6A) of the bores 130 may be, for example, 5 mm. However, depending on the procedure to be performed, and the number of bores to be drilled and their relative positions, any number of channels may optionally be provided, where the channels are arranged at any preselected orientation relative to each other, the bore center points spaced apart any selected distance, and the channels positioned in the body in any selected configuration. For example, in a procedure in which it may be desired to insert four anchors into a bone at positions defining a square shape, a bone drill guiding device may include four parallel channels, the centers of which are configured in a square.

In the embodiment shown, channels 124 resemble cannulas, with a proximal end 138 of each channel 124 extending past the body proximal end 128. However, if desired, the proximal end of the channels may, alternatively, not extend past the body proximal end 128 but, rather, be flush with the body proximal end 128. This may have a potential benefit in that it may provide the device with a wider gripping surface with which to contact the bone.

Figure 7:
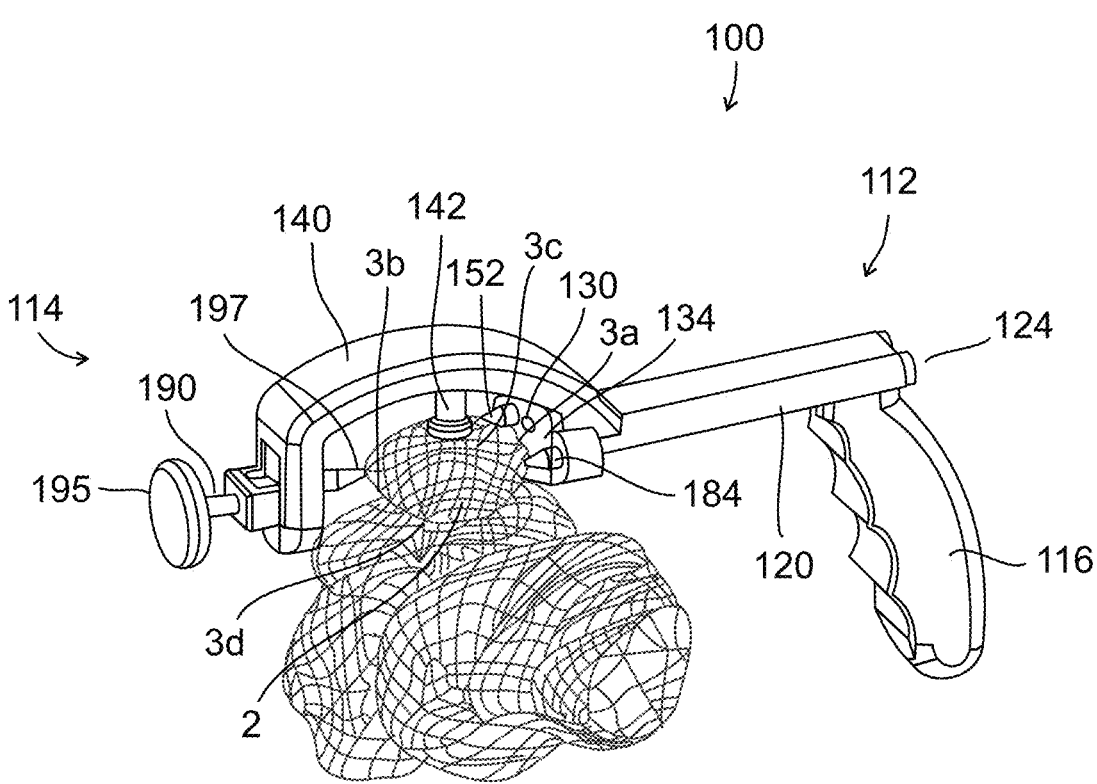
FIG. 7 is a perspective view of a bone drill guiding device shown in FIG. 6A, according to a second embodiment of the invention, the device shown in engagement with a bone.

With additional reference to FIG. 7, the body distal end 126 may be provided with a generally triangular gripping surface 134, seen most clearly in FIG. 6A, suitable for contacting a first side 3a of a bone 2 and preventing the body 120 from moving relative to the bone. As in the embodiment shown, gripping surface 134 may be wider than the distal end 126 of body 120, and may extend both laterally and in a downward direction relative to the body distal end 126. Optionally, gripping surface 134 may not extend outwardly past the side of body 120. Optionally, gripping surface may be narrower than the distal end 126 of body 120. Gripping surface 134 may also be provided with a pair of upper spikes 152 and a lower spike 154, the lower spike being shorter and narrower than each of upper spikes 152. Optionally, each of upper spikes 152 and lower spike 154 may be of the same size. Alternatively, gripping surface 134 may be provided with any suitable number of spikes, positioned in any configuration, for engaging the bone 2 and preventing movement of body 120 relative to the bone. This may have a potential benefit in that the device may better grip a bone having a shape which is not symmetrical relative to the device longitudinal axis. Optionally, lower spike 154 may be configured to engage a lower surface 3d (FIG. 7) of bone 2.

It may be noted that the upper spikes 152 and the lower spike 154 together define an isosceles triangle having an upper base. Optionally, the triangle may be an equilateral triangle. Alternatively, gripping surface 134 may be provided with a single upper spike and a pair of lower spikes that together define an isosceles or equilateral triangle. This may have a potential benefit in providing spikes which may be better positioned for gripping a bone.

In the embodiment shown, upper spikes 152 and lower spike 154 each have an axis (not shown) that may be parallel to the axis 122 of the drill entry portion 112. Alternatively the upper spike and/or lower spikes may have an axis having any other orientation relative to the axis 122 of the drill entry portion 112. This may provide a potential benefit for engaging and securing a bone having a shape which is not symmetrical relative to the device longitudinal axis.

It should also be noted that, additionally in the embodiment shown, upper spikes 152 are located on the gripping surface 134 at positions on either side of the pair of bores 130. Optionally, the upper spikes may be located on the gripping surface 134 at positions between the pair of bores 130.

Optionally, gripping surface 134 may contain no spikes and channels 124 may protrude out of the body distal end 126 (similar to the way the channel proximal ends 138 extend past the body proximal end 128 in FIG. 6B), such that each protruding channel itself provides at least one point for contacting and engaging the first side 3a of the bone. This is discussed further herein.

The drill entry portion 112 and the bone securing portion 114 may be rigidly connected to each other by an arch-shaped coupling element 140 that extends between drill entry portion 112 and bone securing portion 114. Specifically, a proximal end 192 of the arch-shaped element 140 may be connected to a portion of the drill entry portion body 120, just proximal to the gripping surface 134, and a distal end 193 of the arch-shaped element 140 may be connected to a vertical support 180 of the bone securing portion 114. Alternatively, arch-shaped element 140 may be connected at any portion along the drill entry portion body 120, between the body distal end 126 and the body proximal end 128. Alternatively, any suitable connection element may be provided instead of arch-shaped element 140 for connecting the drill entry portion 112 and the bone securing portion 114 together and, in particular, for rigidly connecting the drill entry portion 112 and the bone securing portion 114 together. This may provide a potential benefit in allowing the device to engage a bone while extending around any portions of the bone that may protrude from the bone. Optionally, arch-shaped element 140 may be coupled to the body 120 of the drill entry portion 112 and may be separated from body 120, by any suitable mechanism such as, for example, a snap-fit connection.

Optionally, arch-shaped element 140 may be formed of two separate coupling portions (not shown) which allow the drill entry portion 112 and the bone securing portion 114 to move toward each other. Optionally, the two coupling portions together define a ratchet mechanism similar to that described above with regard to the first embodiment, and shown in FIGS. 2A-4C. While ratchet mechanism 42, shown in FIG. 2D, allows drill entry portion 12 and bone securing portion 14 to be moved axially toward each other, it should be noted that, if desired, device 100 may be provided with a ratchet mechanism including arch-shaped portions that allow the drill entry portion 112 and bone securing portion 114 to move toward each other and to be locked in position when they are in engagement with the bone 2.

Arch-shaped element 140 may be optionally provided with a depending support member 142 which extends downward, from a lower surface 188 of arch-shaped element 140. Support member 142 includes a lower contact surface 144 for contacting and engaging skin adjacent an upper surface 3c of a bone 2 (FIG. 7). As discussed herein, support member 142 may facilitate alignment of the drill entry portion 112 with the first side 3a of the bone 2. Optionally, lower contact surface 144 may have a circular profile and may have a diameter of, for example, 15 mm.

Optionally, the center 132 of each bore 130 positioned approximately 7 mm below the lower contact surface 144. This may ensure that each bore will be drilled into the bone 2 at a location approximately 7 mm below the highest points of the upper surface 3c of the bone.

Optionally, contact surface 144 may be a non-skid surface, for example, a textured surface to securely engage bone upper surface 3c, via the skin, and prevent relative movement between support member 142 and the bone 2 during a surgical procedure. Optionally, support member 142 may be extendable, toward the bone upper surface 3c, and away from bone upper surface 3c, such that the device 100 may be adjusted according to the shape and size of the bone 2. Optionally, support member 142 may be extended and retracted relative to lower surface 188 by rotation of support member 142. This may allow for better engagement between the device 100 and the bone 2, via the skin, and may, be helpful in providing more secure stabilization of the bone relative to the device 100 during a surgical procedure.

Adjacent the body proximal end 128 of the drill entry portion 112, a handle 116 may optionally be rigidly connected, below the body 120. It should be noted that handle 116 may be positioned generally distal to the channel proximal end(s) 138, although the connection between the handle 116 and the drill entry portion 112 is at a location distal to the channel proximal end 138, so as not to interfere with insertion of a drill or other elements into the channel(s) 124. Handle 116 is similar in configuration and function to handle 16 (FIG. 2A), except that handle 116 may not be easily attachable to and detachable from the drill entry portion 112. Alternatively, handle 116 may be attachable to and detachable from the drill entry portion 112. This may have a potential benefit in allowing better visibility of the surgical site and/or allowing better access to the surgical site. Optionally, device 100 may be provided with a smaller handle, optionally at any suitable location on body 120. Optionally, device 100 may include no handle.

The bone securing portion 114 includes a vertical support 180 which extends downward from arch-shaped element 140. Vertical support 180 may be provided with a bore 181, located approximately at a center (not shown) of the vertical support, the bore extending through the vertical support, from a distal side 182 to a proximal side 183 thereof. A u-shaped bracket 191 having a bore 186 may be attached on the distal side 182 of vertical support 180. Bore 181 of vertical support 180 and bore 186 of bracket 191 are axially aligned, and are sized and shaped to receive an adjustable fixation element such as, for example, a screw 190 having an axis 194 which may be parallel to the axis 122 of drill entry portion 112. Optionally, screw 190 and drill entry portion 112 are coaxial.

Bracket 191 and vertical support 180 provide support to screw 190 and retain the screw in the horizontal position shown in FIG. 6B. While bracket 191 is shown as having a u-shaped configuration, optionally, bracket 191 may have any other suitable configuration which supports screw 190.

Screw 190 includes a head portion 195 and a threaded shank 196, with the head portion positioned distally, and a screw tip 197 is positioned proximally, along an axis 194. Screw may be rotatable within bores 181 and 186, whereby rotation in a first direction may move the screw axially and proximally and rotation in a second direction, opposite to the first direction, may move the screw in an axial and distal direction.

It should be noted that, in the embodiment shown, due to relative orientation of the upper spikes, which are parallel to the axis 122 of the drill entry portion 112, and the orientation of the screw 190, both noted above, the tips 184 of upper spikes 152 and the tip 197 of screw 190 together define a triangle having a base between tips 184 of upper spikes 152.

Prior to use, screw 190 may be rotated to move it axially and distally, thereby enlarging a distance between screw tip 197 and tips 184 of upper spikes 152. Screw 190 may be rotated sufficiently to move it distally, to provide sufficient space for locating the bone 2 between the upper spikes 152 and/or the lower spike 154, on one side 3a of the bone 2, and the screw 190, on the other side 3b of the bone 2. In order to securely engage and grip the bone 2, the device 100 may be positioned relative to bone 2 such that arch-shaped element 140 is located above the bone, optionally with support surface 144 of support member 142 in contact with skin adjacent a top surface 3c (FIG. 7) of the bone 2 and at least upper spikes 152 contacting the first side 3a of the bone. The screw 190 may be rotated and moved proximally, until the screw tip 197 engages the second side 3b of the bone 2, via skin adjacent the second side of the bone. Optionally, lower spike 154 may engage side 3a of the bone or may engage a lower side 3d of the bone.

It should be noted that, in the embodiment shown, the pair of upper spikes 152 each provides a contact point between the drill entry portion 112 and the bone 2, on side 3a of the bone, and the screw tip 197 provides a contact point between the bone securing portion 114 and the bone (or skin adjacent the bone), on side 3b of the bone.

Additionally, the upper spikes 152 and the screw 190 are positioned relative to each other such that they define contact points positioned in the shape of an isosceles triangle, with a base on the first side 3a of the bone 2. Optionally, the triangle defined may be in a horizontal plane.

The optional support member 142 may provide further contact between the device 100 and skin adjacent the bone 2, as discussed above, specifically on skin adjacent the upper side 3c of the bone, which provides additional stability, thereby preventing movement of the bone 2 during a surgical procedure. Further, lower spike 154 may provide yet further contact with the bone, at a lower surface 3d thereof. However, as noted above with regard to device 10 (FIGS. 2A-5C), device 100 is specifically designed such that there are a minimum of three contact points between the device and the bone 2 (and/or skin adjacent the bone).

The at least three contact points may include at least two contact points between the drill entry portion 112 and the bone first side 3a, for example, provided by upper spikes 152, and at least one contact point between the bone securing portion 114 and skin adjacent the bone second side 3b, provided by screw 190. Alternatively, in some embodiments, the at least three contact points may include at least one contact point between the drill entry portion 112 and the bone first side 3a, and at least two contact points between the bone securing portion 114 and skin adjacent the bone second side 3b.

Provision of at least three contact points, located on at least two opposite sides of the bone 2 (and/or skin adjacent the bone) may provide the device 100 with stability relative to the bone, allowing the bone to be securely gripped during a surgical procedure such as, for example, drilling into the bone and/or anchor insertion, as discussed herein. Further contact points between the device 100 and the bone (and/or skin adjacent the bone), as noted above, may provide further stability, as discussed herein.

Figure 8A:
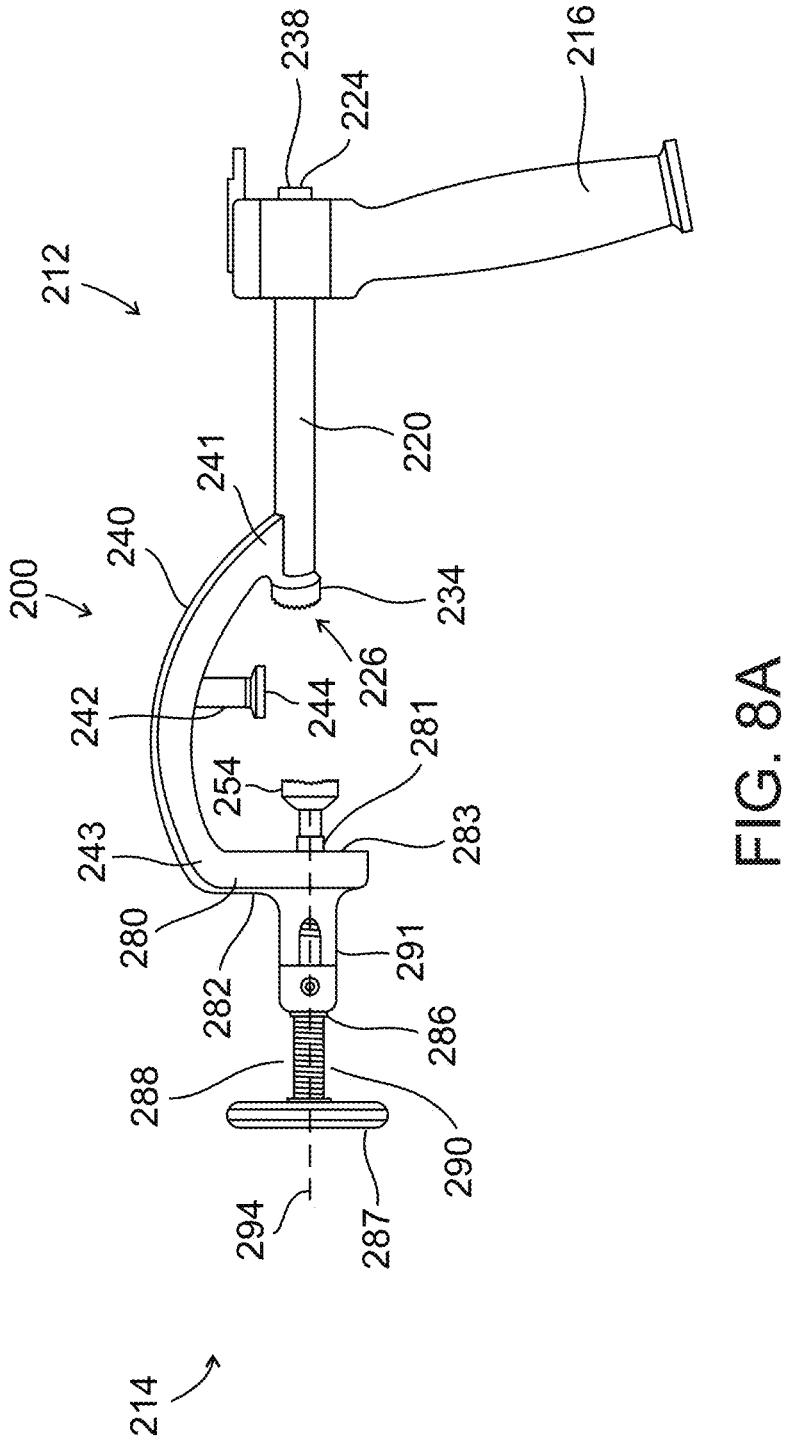
FIG. 8A is a side view of a bone drill guiding device, according to a third embodiment of the invention.
Figure 8B:
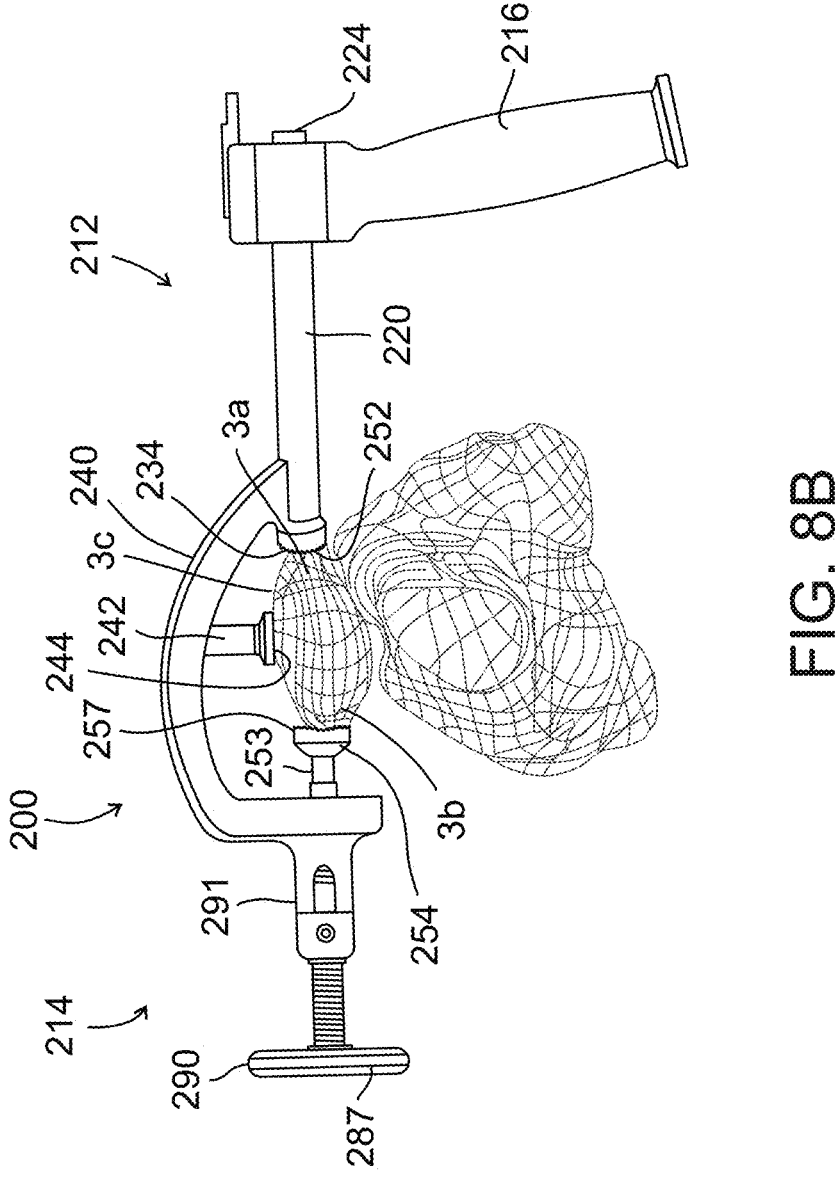
FIG. 8B illustrates the device of FIG. 8A, according to the third embodiment of the invention, the device shown engaged with a bone.
Figure 8C:
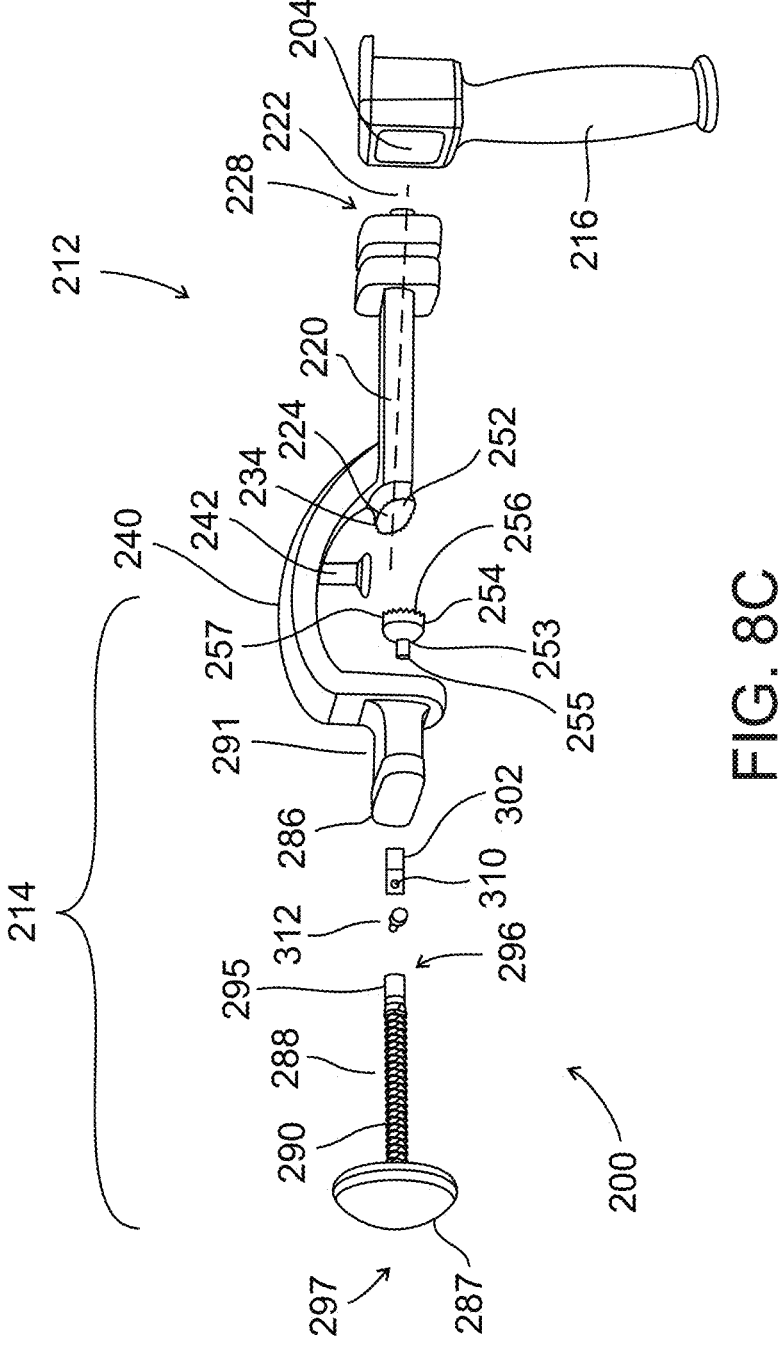
FIG. 8C is an exploded view of the device shown in FIG. 8A, according to the third embodiment of the invention.

With reference to FIGS. 8A and 8C there is shown a bone drill guiding device 200 according to a third embodiment of the invention. As some of the components of device 200 are similar in configuration and function to similar components of the first and/or second embodiment of the device, described hereinabove, they will not be described again in detail.

Device 200 includes a drill entry portion 212, for engaging a first side of bone and via which a drill may be guided relative to the first side of a bone; and a bone securing portion 214 for engaging a second side 3*b* of the bone 2. Drill entry portion 212 and bone securing portion 214 together provide at least three contact points between the device 100 and the bone 2 and/or skin adjacent the bone.

Figure 9A:
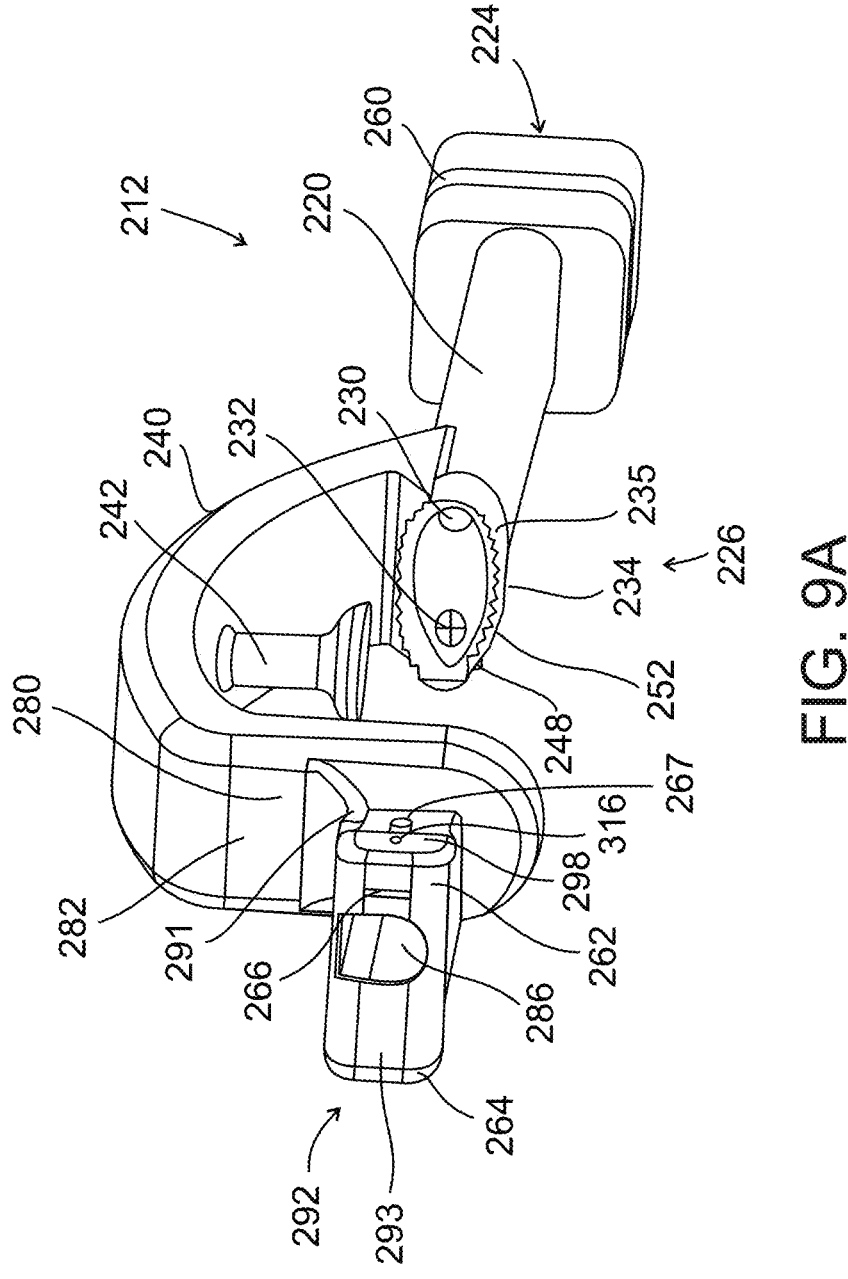
FIGS. 9A and 9B are respective side-perspective and bottom-perspective views of a guide portion of the device of FIG. 8C, according to the third embodiment of the invention.
Figure 9B:
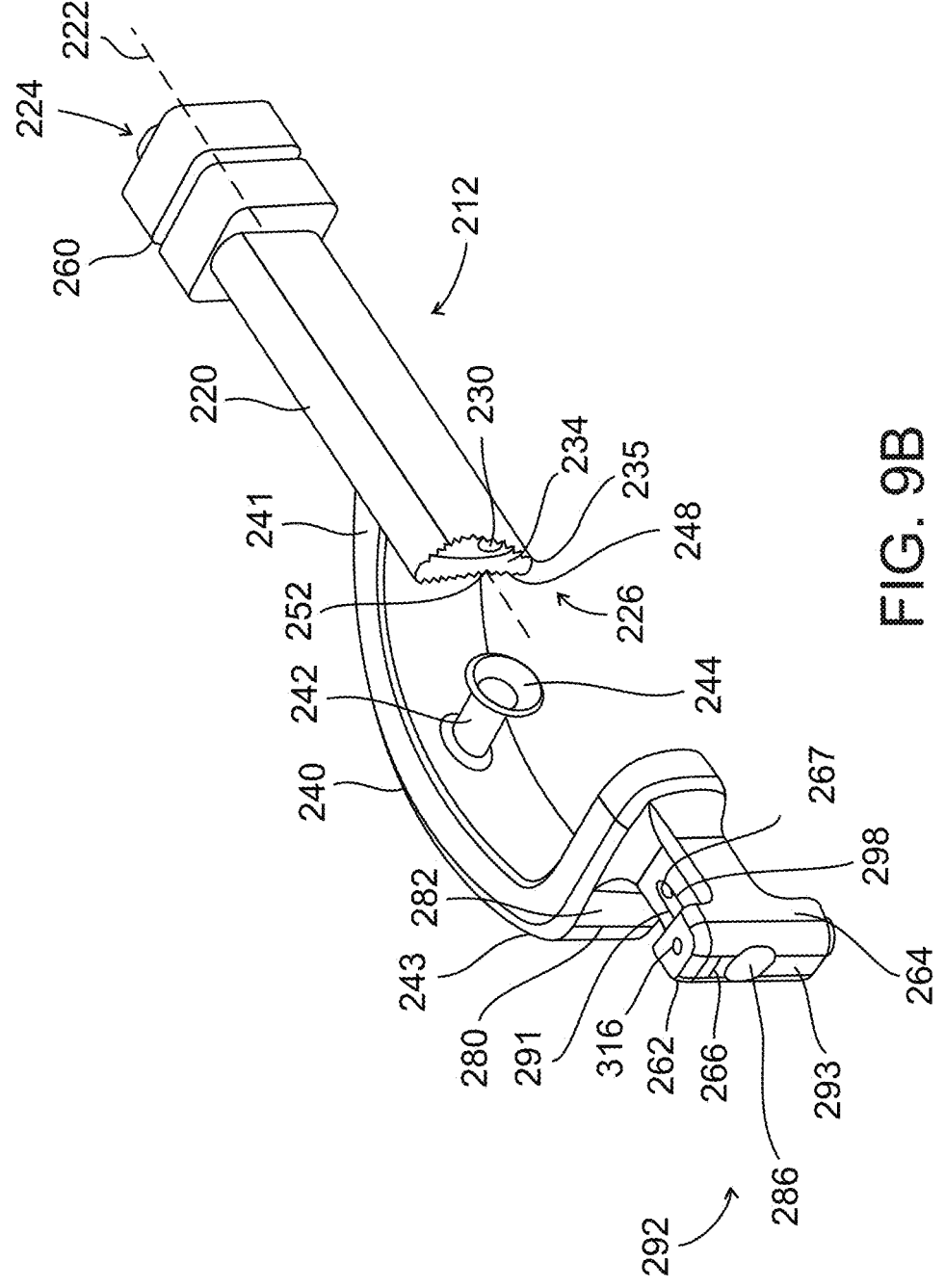

Drill entry portion 212 has an elongate body 220 having a longitudinal axis 222, shown most clearly in FIG. 9B. Body 220 includes at least one channel 224 extending therethrough, from a proximal end 228 of the body 220 to a distal end 226 of the body 220. Each channel 224 has a bore 230 extending therethrough (FIG. 9A). Each channel 224 is sized to receive a bone drill therethrough, as discussed further herein.

In the embodiment shown in FIGS. 8A-C, the drill entry portion 212 may be provided with two channels 224 which are parallel to axis 222. The distance between the center points 232 (FIG. 9A) of the bores 230 may be, for example, about 5 mm. However, it should be noted that, depending on the procedure to be performed, any number of channels may be provided, where the channels are arranged at any preselected orientation relative to each other, the bore center points spaced apart any selected distance, and the channels positioned in the body in any selected configuration. For example, in a procedure in which it may be desired to insert four anchors into a bone at positions defining a square shape, a bone drill guiding device may include four parallel channels, the centers of which are configured in a square.

As illustrated in FIG. 8A, channels 224 resemble cannulas, with a proximal end 238 of each channel 224 extending past the body proximal end 228. However, it should be noted that, if desired, the proximal end of the channels may, alternatively, not extend past the body proximal end 228 but, rather, be flush with the body proximal end 228.

With additional reference to FIGS. 8B and 9A-B, the body distal end 226 may be provided with a first gripping element 234, suitable for contacting a first side 3*a* of a bone 2 and preventing the body 220 of the drill entry portion 212 from moving relative to the bone.

In the embodiment shown First gripping element 234 optionally may have a generally cylindrical shape with an open end facing distally, and gripping element 234 may optionally have an oval cross-sectional profile 235 (FIG. 9A), taken in a plane perpendicular to axis 222. Alternatively, the first gripping element 234 may have any other suitable cross-sectional profile, for example, circular. This may have a potential benefit in that the first gripping element 234 may concentrate more gripping force on a smaller area of the bone, first gripping element 234 may be positioned at the end of body 220 such that channel bores 230 are located within the oval cross-sectional profile 235. First gripping element 234 may also be provided with a plurality of teeth 252 which include edges 248 directed distally. Teeth 252 are sized and shaped to engage and grip the first side 3*a* of a bone 2 (FIG. 8B) and to prevent movement of body 220 relative to the bone. The provision of a first gripping element 234 as described herein may provide a component for gripping a bone without causing damage to meniscus located in the area of the bone, as compared with other types of gripping elements.

Optionally, drill entry portion 212 may not include a first gripping element 234 and instead, channels 224 may protrude out of the body distal end 226 in a manner similar to that discussed with regard to the second embodiment, such that each protruding channel itself provides at least one point for contacting and engaging the first side 3*a* of the bone. This is discussed further herein.

The drill entry portion 212 and the bone securing portion 214 may be rigidly connected to each other by any suitable means. In the embodiment shown, drill entry portion 212 and bone securing portion 214 are rigidly connected to each other by an arch-shaped coupling element 240 that extends between drill entry portion 212 and bone securing portion 214. Specifically, a proximal end 241 of the arch-shaped element 240 may be connected to a portion of the drill entry portion body 220, just proximal to the first gripping element 234, and a distal end 243 of the arch-shaped element 240 may be connected to a vertical support 280 of the bone securing portion 214. Alternatively, arch-shaped element 240 may be connected at any portion along the drill entry portion body 220, between the body distal end 226 and the body proximal end 228. It should also be noted that, alternatively, any suitable connection element may be provided instead of arch-shaped element 240 for connecting the drill entry portion 212 and the bone securing portion 214 together and, in particular, for rigidly connecting the drill entry portion 212 and the bone securing portion 214 together. Optionally, arch-shaped element 240 may be coupled to the body 220 of the drill entry portion 212 and may be separated from body 220, by any suitable mechanism such as, for example, a snap-fit connection.

As discussed above with regard to the second embodiment of the invention, optionally, arch-shaped element 240 may be formed of two separate coupling portions (not shown) which allow the drill entry portion 212 and the bone securing portion 214 to move toward each other and to be locked in position when they are in engagement with the bone 2.

Arch-shaped element 240 may be optionally provided with a depending support member 242 for contacting skin adjacent a third side 3*c* of the bone 2, whereby support member 242 may be similar in structure and function to support member 142 described herein with regard to the second embodiment (FIG. 6A) and will not, therefore, be discussed here in further detail. As discussed herein, support member 242 may facilitate alignment of the drill entry portion 212 with the first side 3*a* of the bone 2. Optionally, support member 242 may be adjustable such that it may be moved toward and away from the bone, to provide better contact on the third side 3*c* of the bone 2.

Device 200 may be provided with a handle 216 which may be selectably connected to the drill entry portion 212, adjacent the body proximal end 228. Handle 216 may be an elongate element including a generally elongate portion 206 configured to be gripped by a user during a surgical procedure. Handle elongate portion 206 may be provided, at a lower end 219 thereof, with a base 208, which may be wider than the remainder of the handle 216. Base 208 may be provided to allow the handle 216 to be maintained in an upright position, for example, when placed upon a table (not shown) with the handle 216 in a generally vertical orientation.

An upper end 218 of handle elongate portion 206 may include a generally square-shaped portion 202 having a generally square-shaped opening 204 which extends through the handle 216 from a proximal side 215 thereof to a distal side 217 thereof. Opening 204 has a proximal side 227 and a distal side 229. Opening 204 may be sized and shaped for receiving a proximal end 228 of body 220. Opening 204 defines an inner surface 210, the inner surface 210 extending around the opening 204. Handle portion 202 may be also provided with a lever 201 connected to inner surface 210. The lever 201 has a proximal end 211 which extends proximally out of opening 204 and a distal end 213 disposed within opening 204, between the opening proximal side 227 and the opening distal side 229. Lever distal end 213 may be provided with a protrusion 205 which may be biased radially inward relative to inner surface 210.

Body proximal end 228 has a generally square cross-sectional profile and may be optionally wider than the body distal end 226. Optionally, body proximal end 228 has a narrower cross-sectional profile than that of the body distal end 226. Optionally, the cross-sectional profile of body proximal end 228 may not be narrower than that of body distal end 226. Body proximal end 228 may be provided with a groove 260 that extends around the periphery of the body proximal end 228.

Figure 8D:
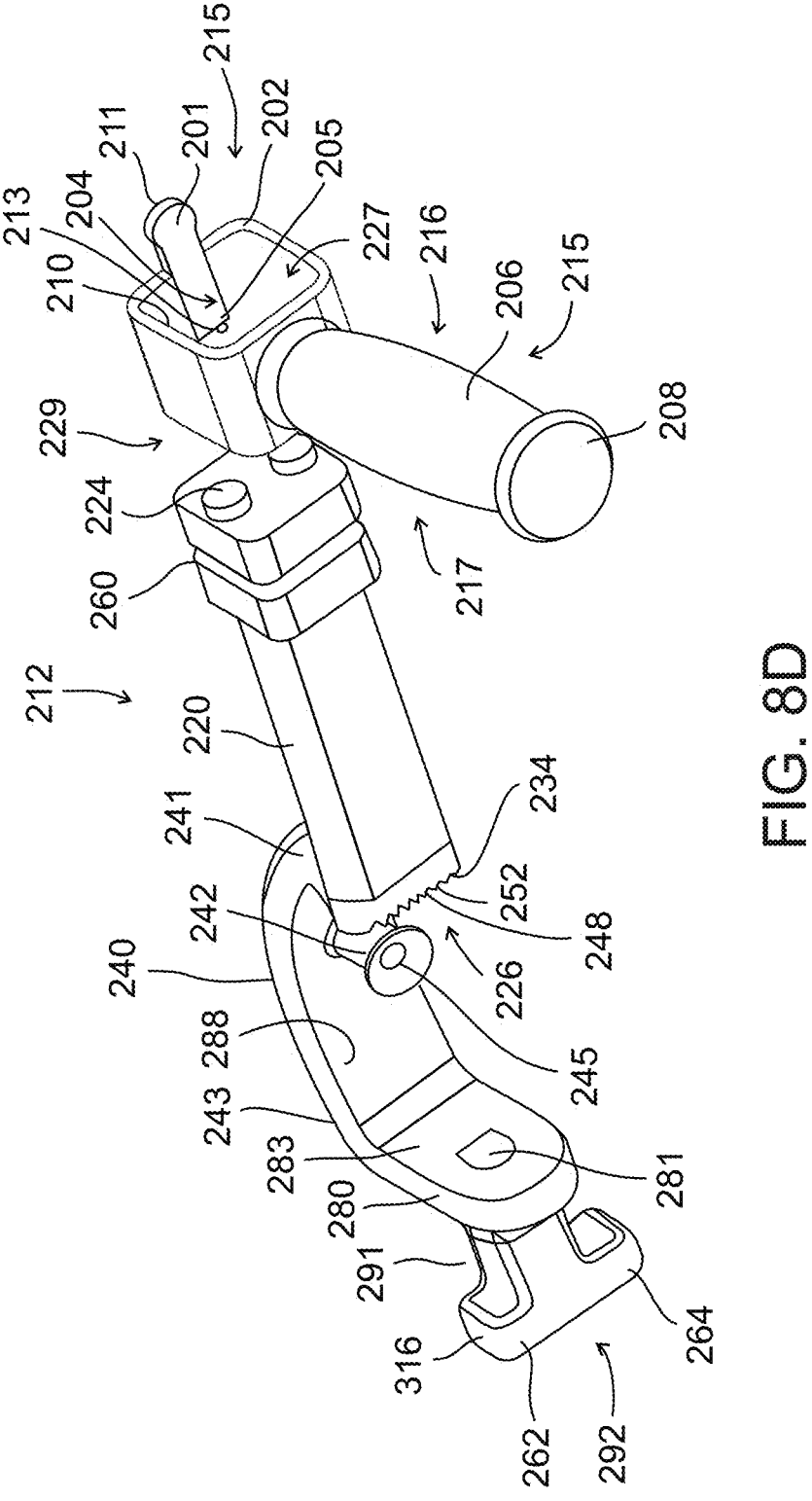
FIG. 8D is an exploded view of the guide portion and handle shown in FIG. 8C, the view taken in perspective from the bottom and side, according to the third embodiment of the invention.

When the body proximal end 228 and the handle 216 are oriented and aligned as in FIG. 8D, body proximal end 228 may be moved toward the opening 204 in handle 216 until body proximal end fits into the distal side 229 of opening 204. Once body proximal end 228 has been inserted far enough into opening 204 such that it contacts the protrusion 205 it may apply force to the protrusion 205 in the direction of inner surface 210, thereby forcing lever 201 to be deflected downward. Protrusion 205 may be slidable over the body proximal end 228. When protrusion 205 reaches groove 260 it will be biased downward, into the groove, and lever 201 will be released and may move upward. This provides a snap-fit connection between the handle 216 and the drill entry portion 212 which may retain these components connected to each other.

When it is desired to separate the handle 216 from the drill entry portion 212, the lever proximal end 211 may be depressed, thereby releasing protrusion 205 from groove 260 and allowing the body proximal end 228 to be slid out of the handle opening 204.

It should be noted that the body proximal end 228 and the handle upper portion 218 have corresponding generally square-shapes, and that groove 260 extends around the entire periphery of body proximal end 228. Therefore, the handle may be attached to the drill entry portion 212 at any one of four different orientations, namely, with the handle elongate portion 206 positioned below the drill entry portion 212 (as shown in FIG. 8A), above the drill entry portion 212, or to either side of the drill entry portion 212.

It should be noted that the provision of selectable orientations of the handle 216 relative to the drill entry portion 212 allows selection of a particular orientation depending on the particular procedure to be performed, physical structure of the surgical site, and personal preference of the surgeon.

While the third embodiment of the present invention may be described as having a groove 260 on the body proximal end 228 and a protrusion 205 in the handle opening 204 which allow the handle to be retained on the body proximal end, it should be noted that, alternatively, any other suitable mechanism may be provided for attaching the handle 216 and drill entry portion 212 and maintaining a connection therebetween such as, for example, that shown with regard to the first embodiment (FIG. 2D). Alternatively, a device in accordance with the invention may include a handle that may be permanently attached to the drill entry portion, for example, as described with regard to the second embodiment.

It should also be noted that handle 216 is shown, for example, in FIG. 8A, as being positioned distal to the channel proximal end(s) 238, so as not to interfere with insertion of a drill or other elements into the channel(s) 124.

Alternatively, device 200 may include any other suitable type of handle on drill entry portion 212. Optionally, device 200 may not include a handle on the drill entry portion 212.

As noted above, bone securing portion 214 includes a vertical support 280 which extends downward from arch-shaped element 240. Vertical support 280 may be provided with a bore 281, approximately at a center (not shown) of the vertical support, the bore extending through the vertical support, from a distal side 282 to a proximal side 283 thereof. The distal side 282 of vertical support 280 may be provided with an extension 291 having a bore 286. Bore 281 of vertical support 280 and bore 286 of extension 291 are aligned, and are sized and shaped to receive an adjustable fixation element such as, for example, a screw 290 having a second gripping element 254 connected thereto, the screw 290 and second gripping element 254 both positioned along an axis 294. Optionally, axis 294 may be parallel to the axis 222 of drill entry portion 212. Optionally, screw 290 and drill entry portion 212 are coaxial.

Second gripping element 254 optionally has a generally cup-shaped configuration with a proximally-facing open end, and having a proximally-facing surface 256 provided with a plurality of teeth 257. Second gripping element 254 may optionally have a generally cylindrical shape, and may optionally have a circular cross-sectional profile, taken in a plane perpendicular to axis 222. Alternatively, the second gripping element 254 may have any other suitable cross-sectional profile, for example, oval. This may have a potential benefit in that the first gripping element 234 may concentrate more gripping force on a larger area of the bone.

Teeth 257 of second gripping element 254 are to be directed proximally for engaging skin (not shown) adjacent a second side 3b of a bone 2, to thereby engage and grip the second side 3b of the bone 2 (FIG. 8B). Second gripping element 254 also includes a neck 253 extending distally relative to teeth 257, the neck 253 having a bore 255 formed therein.

The provision of a second gripping element 254 as described herein may provide a component for gripping a bone without causing damage to meniscus located in the area of the bone, as compared with other types of gripping elements.

Extension 291 may be provided with a widened distal portion 292. Distal portion 292 has a distal face 293 and includes a pair of finger grips 262 and 264 which extend laterally relative to extension 291. In the embodiment of FIG. 9B, finger grip 264 extends further laterally than does finger grip 262. However, if desired, finger grips 262 and 264 may have any desired length and may optionally be of the same length. A slot 266 may be provided on distal face 293, the slot extending into the interior of the extension 291. Extension 291 may have a lateral outer surface 298 in which there may be an elongate aperture 267.

With additional reference to FIG. 8C, screw 290 includes a head portion 287 at the screw distal end 297, a threaded shank 288, and a narrow portion 295 adjacent the screw proximal end 296.

In order to assemble the bone securing portion 214, screw proximal end 296 may be inserted through bore 286 in extension 291 and through bore 281 in vertical support 280, such that the screw proximal end 296 extends through vertical support 280. The second gripping element 254 may be attached to the screw proximal end 296 by inserting the narrow screw portion 295 into bore 255 in the second gripping element 254. Alternatively, the neck 253 of the second gripping element 254 may be inserted into the narrow portion 295 of the screw 290.

Once the bone securing portion 214 has been assembled, the screw 290 may be rotatable within bore 281 in vertical support 280 and bore 286 in extension 291, whereby rotation of screw 290 in a first direction may move the screw and the attached second gripping element proximally and rotation of screw 290 in a second direction, opposite to the first direction, may move the screw and the attached second gripping element 254 in a distal direction. Such movement changes a distance between first gripping element 234 and second gripping element 254, as discussed further herein.

Figure 10:
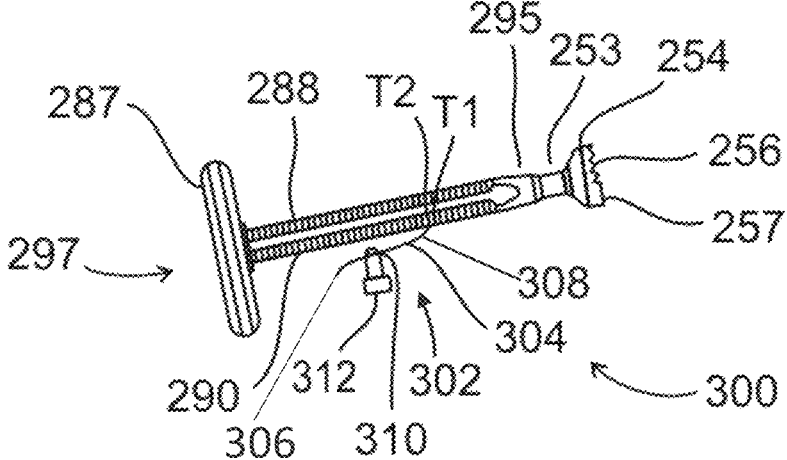
FIG. 10 is a top view of a locking mechanism of the bone securing portion of the device of FIG. 8A, according to the third embodiment of the invention.

With further reference to FIG. 10, device 200 may be provided with a one-way locking mechanism 300 for maintaining the distance between the first gripping element 234 and the second gripping element 254. Optionally, locking mechanism 300 may include any type of ratchet mechanism, as known in the art. Specifically, in the embodiment shown, locking mechanism 300 includes a locking screw 312 and a locking element 302 the latter of which, in the embodiment shown, may be an elongate flexible portion 304 having a first end 306 and a second end 308. Adjacent the first end 306 of locking element 302 there may be disposed a bore 310.

Second end of locking element 302 may be inserted into slot 266 (FIG. 9B) such that it extends into the interior of the extension 291. The locking element 302 will then be visible at aperture 267 and may be advanced further into the interior of the extension 291 until second end 308 of locking element 302 engages the screw thread 289 between threads T1 and T2 (FIG. 10). Locking screw 312 may then be inserted first into a bore 316 in extension 291 and then into bore 310 (FIG. 8C) in locking element 302, to activate the locking mechanism 300. By rotating locking screw 312 clockwise, locking screw 312 tightens against locking element 302, thereby forcing locking element 302 further into the space between threads T1 and T2.

Rotation of screw head 287 in a clockwise direction will cause the screw shank 288 to rotate within extension 291 (FIG. 9B), thereby causing the second gripping element 254 to move toward the first gripping element 234. Due to flexibility of the locking element 254, as the shank 288 is rotated a complete revolution, the locking element will bend slightly and the second end 308 of the locking element will slide out of the space between threads T1 and T2, move over thread T2, and settle in the adjacent space (next to T1). By continuing to rotate the screw head 287 clockwise, the second gripping element 254 may be moved a selected distance toward the first gripping element 234.

In order to release the screw 290, so that it may be rotated in a counterclockwise direction, thereby moving the second gripping element 254 away from the first gripping element 234, the locking screw must be removed, thereby allowing locking element 302 to move out from between threads of the screw 290 and slide over the threads as the shank 288 is rotated counterclockwise.

Prior to use, locking screw 312 may be loosened so that screw 290 may be rotated to move it axially and distally, thereby enlarging a distance between teeth 257 of the second gripping element 254 and teeth 252 of the first gripping element 234. Screw 190 may be rotated in a first direction a sufficient amount to provide ample space for locating the bone 2 between the first gripping element 234 and the second gripping element 254. Locking screw 312 may then be tightened, thus preparing the locking mechanism 300 for tightening the device relative to the bone 2.

In order to securely grip the bone 2, the device 200 may be positioned relative to bone 2 such that arch-shaped element 240 may be located above the bone, optionally with a support surface 244 of support member 242 in contact with skin adjacent a top surface 3*c* (FIG. 8B) of the bone 2. The first gripping element 234 may be positioned adjacent the first side 3*a* of the bone 2. Screw head portion 287 may then be rotated in a second direction, opposite to the first direction, to rotate screw 290, thereby moving the second gripping element 254 toward the second side 3*b* of the bone 2. As screw 290 is rotated, locking mechanism 300 allows further rotation of the screw 290 in a clockwise direction, as discussed above, thereby allowing the second gripping element 254 to be moved toward the first gripping element 234, Rotation of screw head portion 287 is continued until second gripping element 254 engages skin adjacent the second side 3*b* of the bone 2.

Optionally, any or all of the contact points may be locked in position when in engagement with the bone (or skin adjacent the bone). A potential benefit provided by the contact points is that they may allow the device to be secured relative to the bone prior to drilling into the bone, and the secure contact may be maintained throughout procedures such as drilling and anchor insertion. A device according to embodiments of the present invention may allow such securing of the device relative to a bone such as, for example, as may be useful when drilling into a bone such as a patella, which typically has a size and shape that may be stabilized relative to a drill to ensure that it does not move during the procedure.

It should be noted that, in the third embodiment shown, the first and second gripping elements 234 and 254 provide at least three contact points between the device 200 and the bone 2 and/or skin adjacent the bone. The three contact points include at least one contact point between the drill entry portion 212 and the first side 3*a* of the bone 2 and at least one contact point between the bone securing portion 214 and skin adjacent the second side 3*b* of the bone 2. Additionally, as noted above, the optional support member 242 may provide further contact between the device 200 and the bone 2, as discussed above, specifically on skin adjacent the upper side 3*c* of the bone, which provides additional stability, thereby preventing relative movement between device 200 and the bone 2 during a surgical procedure.

However, as noted above with regard to device 10 (FIGS. 2A-5C), device 200 may be specifically designed such that there are provided a minimum of three contact points between the device and the bone 2 (and/or skin adjacent the bone). The at least three contact points may include at least two contact points between the drill entry portion 212 and the bone first side 3*a*, for example, provided by first gripping element 234, and at least one contact point between the bone securing portion 214 and skin adjacent the bone second side 3*b*, provided by the second gripping element 254. Optionally, the first gripping element 234 may provide at least two contact points between the drill entry portion 212 and the bone first side 3*a*, the at least two contact points being spaced apart a distance of up to, for example, 25 mm, at opposite ends of the oval cross-sectional profile 235 (FIG. 9A). Alternatively, in some embodiments, the at least three contact points may include at least one contact point between the drill entry portion 212 and the bone first side 3*a*, and at least two contact points between the bone securing portion 214 and skin adjacent the bone second side 3*b*. Optionally, the second gripping element 254 may provide at least two contact points between the bone securing portion 214 and the bone second side 3*b*, the at least two contact points being spaced apart a distance of up to, for example, 14 mm, at opposite sides of the second gripping element 254.

Provision of at least three contact points, located on at least two opposite sides of the bone 2 (and/or skin adjacent the bone) may provide the device 200 with stability relative to the bone, allowing the bone to be securely gripped during a surgical procedure such as, for example, drilling into the bone and/or anchor insertion, as discussed herein. Further contact points between the device 200 and the bone (and/or skin adjacent the bone), noted above, may provide further stability, as discussed herein.

With reference to FIGS. 16A-D there is shown a bone drill guiding device 500 according to a fourth embodiment of the invention. As some of the components of device 500 are similar in configuration and function to similar components of the first, second, and/or third embodiment of the device, described hereinabove, they will not be described again in detail.

Device 500 includes a drill entry portion 512, for engaging a first side of bone and via which a drill may be guided relative to the first side of a bone; and a bone securing portion 514, for engaging a second side 3b of the bone 2. Drill entry portion 512 is provided with a first gripping element 534 and bone securing portion 514 is provided with a second gripping portion 254, both of which will be discussed further hereinbelow, which together provide at least three contact points between the device 500 and a bone 2 and/or skin adjacent the bone.

Figure 16A:
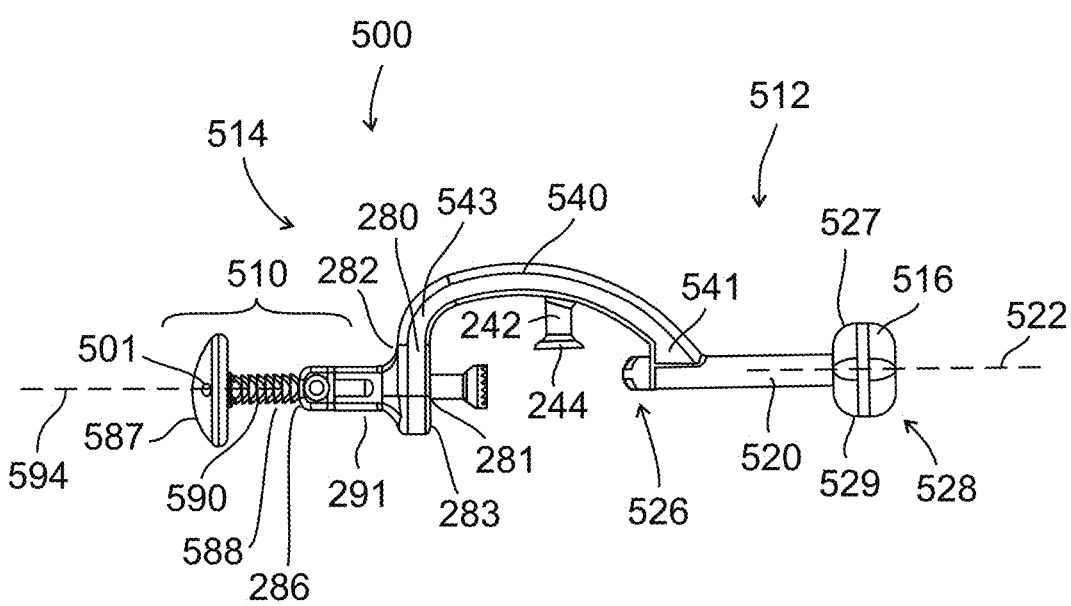
FIG. 16A is a side view of a device according to a fourth embodiment of the prevent invention.

Drill entry portion 512 has an elongate body 520 having a longitudinal axis 522, shown most clearly in FIG. 16A. Body 520 includes at least one channel 524 (FIGS. 16C and 17) extending therethrough, from a proximal end 528 of the body 520 to a distal end 526 of the body 520. Each channel 524 has a bore 530 extending therethrough. Each channel 524 is sized to receive a bone drill therethrough, as discussed herein, with reference to devices 10, 100, and 200.

Figure 16B:
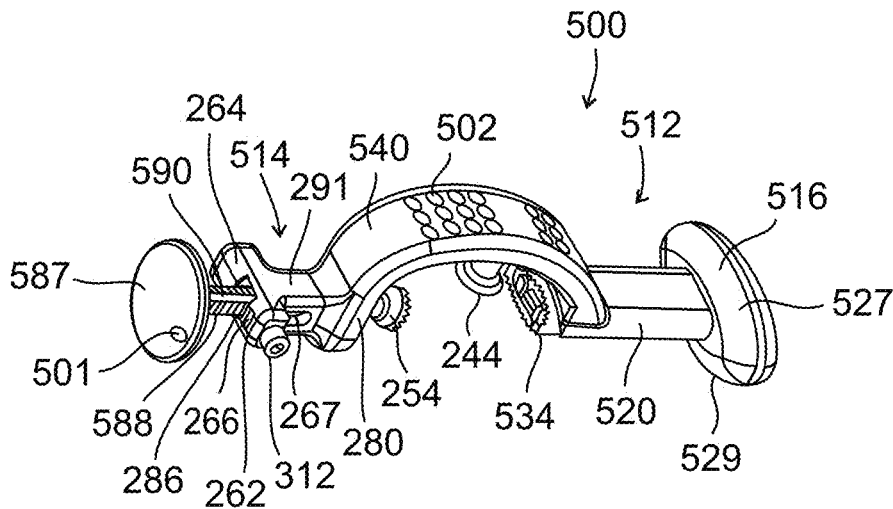
FIG. 16B is a perspective view of the device according to the fourth embodiment.
Figure 16C:
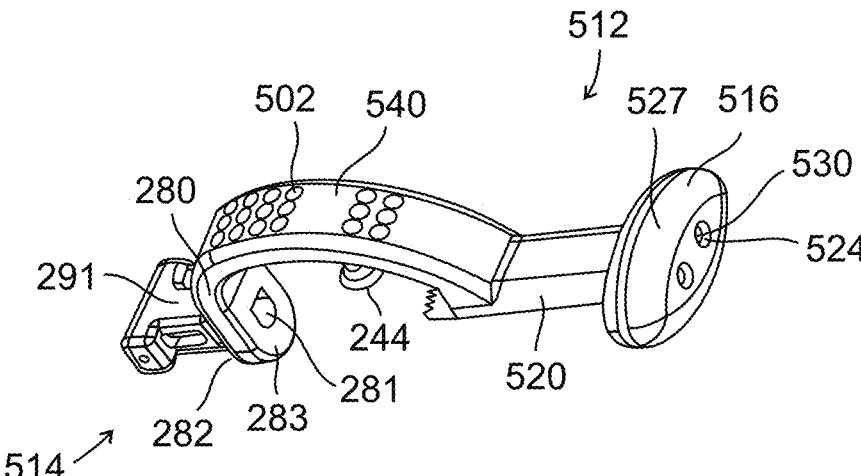
FIG. 16C is a perspective view of the device according to the fourth embodiment, with the fixation element removed for the sake of clarity.
Figure 16D:
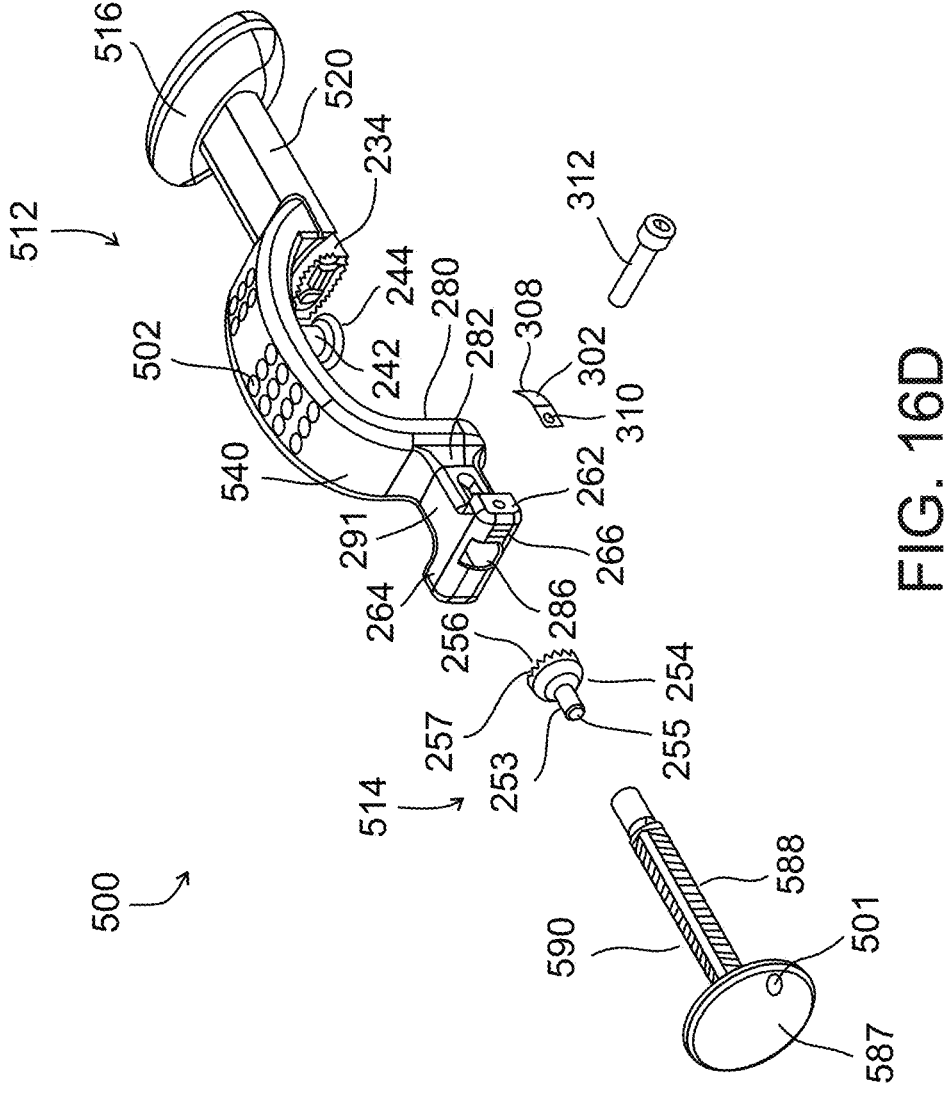
FIG. 16D is an exploded view of the device according to the fourth embodiment of the present invention.
Figure 17:
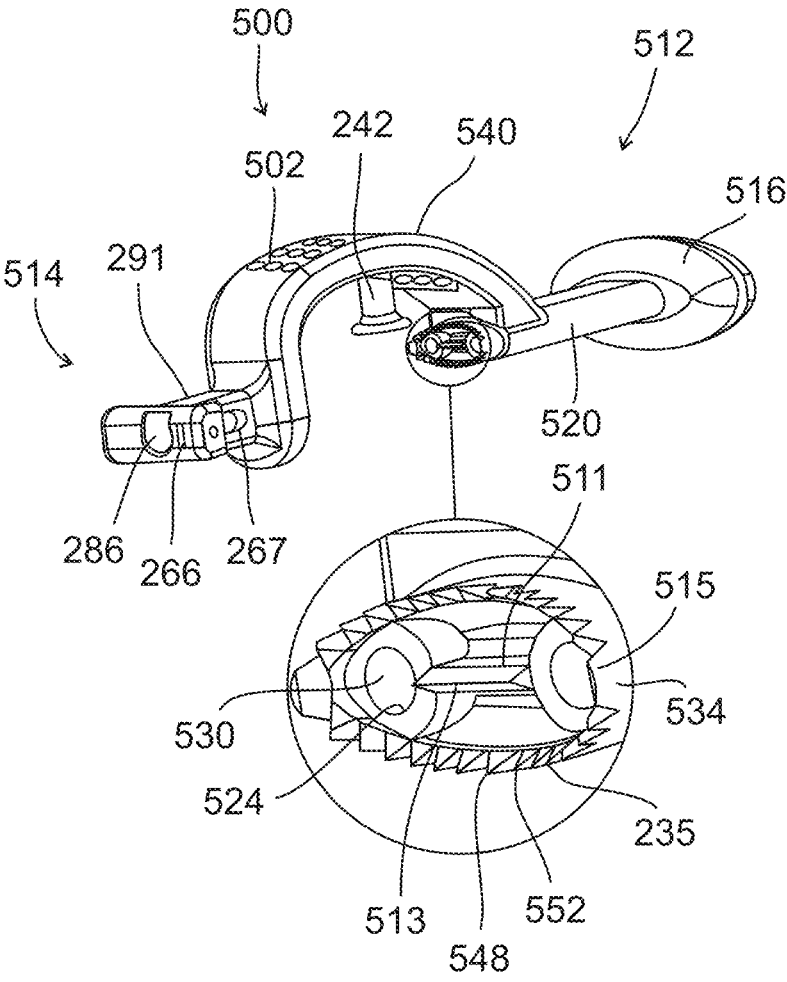
FIG. 17 is a perspective view of the device according to the fourth embodiment, where the fixation element has been removed, for the sake of clarity, and with a portion of the device enlarged to show details thereof.

In the embodiment shown in FIGS. 16A-17, the drill entry portion 512 may be provided with two channels 524 which are parallel to axis 522. The distance between the center points 232 of the bores 530 may be, for example, about 5 mm. However, depending on the procedure to be performed, any number of channels may be provided, where the channels are arranged at any preselected orientation relative to each other, the bore center points spaced apart any selected distance, and the channels positioned in the body 520 in any selected configuration. For example, in a procedure in which it may be desired to insert four anchors into a bone at positions defining a square shape, a bone drill guiding device 500 may include four parallel channels, the centers of which are configured in a square.

As illustrated in FIGS. 16C and 17, channels 524 resemble cannulas, optionally (not shown) with a proximal end of each channel 524 extending past the body proximal end 528. However, it should be noted that, if desired, the proximal ends of the channels may, alternatively, not extend past the body proximal end 528 but, rather, be flush with the body proximal end 528.

With additional reference to FIG. 17, the body distal end 526 may be provided with a first gripping element 534, suitable for contacting a first side 3a of a bone 2 and preventing the body 520 of the drill entry portion 512 from moving relative to the bone. First gripping element 534 has a generally cylindrical shape with an open end facing distally, and first gripping element 534 may have an oval cross-sectional profile 235, taken in a plane perpendicular to axis 522. Alternatively, the first gripping element 534 may have any other suitable cross-sectional profile, for example, circular.

In the embodiment shown, first gripping element 534 may be positioned at the end of body 520 such that channel bores 530 are located within the oval cross-sectional profile 235. First gripping element 534 may also be provided with a plurality of teeth 552 which include edges 548 directed distally. Teeth 552 are sized and shaped to engage and grip the first side 3a of a bone 2 (FIG. 19) and to prevent movement of body 520 relative to the bone. The provision of a first gripping element 534 having a plurality of small teeth 552, as described herein, may provide a component for gripping a bone without causing damage to meniscus located in the area of the bone, as compared with other types of gripping elements. Optionally, first gripping element 534 includes at least one protrusion 515 which extends distally from the oval cross-sectional profile 235. Optionally, the at least one protrusion 515 extends further distally than teeth 552, to provide additional points for gripping the bone 2.

Optionally, drill entry portion 512 may not include a first gripping element 534 and instead, channels 524 may protrude out of the body distal end 526 in a manner similar to that discussed with regard to the second embodiment of the invention, such that each protruding channel itself provides at least one point for contacting and engaging the first side 3a of the bone. This is discussed further herein.

Optionally, within the oval cross-sectional profile 235 there is provided a horizontal rib 511 between channels 524. Rib 511 is preferably equidistantly located between channels 524. Rib 511 may optionally extend distally past teeth 552 and past distal ends 504 of channels 524. The distalmost portion of rib 511 may include a sharpened edge 513. When device 500 grips a bone 2, with first gripping element 534 engaged with a first side 3a of the bone (FIG. 19), rib 511 may be pressed against the bone, causing a small scratch or indentation in the bone. Rib 511 thereby acts as a marker, leaving a marking on the bone at a location between the drilled bores. Since the rib 511 may be equidistantly located between channels 524, it may leave a marking on the bone, whereby the marking is laterally symmetric relative to the drilled bores.

This marking may be useful, for example, in a procedure in which the device 500 is utilized to guide drilling of bores, after which the device is disengaged from the bone 2 prior to insertion of anchors. By marking the bone at a location between the drilled bores, the surgeon can more easily locate the drilled bores after the device has been removed from the surgical site. This may be especially useful in procedures in which the drilled bores are very small and/or in which the surgical site includes debris which may obscure the surgeon's view of the surgical site. Optionally, the marking is a tactile marking. This may facilitate location of the drilled bores by a surgeon when the surgical site is obscured by surgical debris. Optionally, the marking includes multiple markings.

Optionally, drill entry portion 512 may be provided with a marker having an alternative configuration such as, for example, an X, a cross, or a circle. This may have a potential benefit in that the mark provided on the bone may be rotationally symmetric. This may further facilitate locating the drilled bores. This may also facilitate repositioning of device 500, with the channel(s) 524 aligned with the drilled bore(s) if the device has been disengaged from the bone 2. Optionally, the marker may be configured as a dot, which might least interfere with positioning of the device.

The drill entry portion 512 and the bone securing portion 514 are rigidly connected to each other by an arch-shaped coupling element 540 that extends between drill entry portion 512 and bone securing portion 514. Arch-shaped coupling element 540 may have any suitable width, such as, for example, 24 mm. Arch-shaped coupling element 540 may be provided with a plurality of holes 502 at any location therein, for example, at a central portion of the arch-shaped coupling element or along the entire length of the arch-shaped coupling element. Optionally, holes 502 may be arranged in rows and/or columns, for example, as shown in FIG. 16C, along any portion of the arch-shaped coupling element 540. Holes 502 may facilitate viewing of the surgical area and/or may enable better viewing of the surgical area by allowing light to shine through the holes and onto the surgical area. Optionally, holes 502 may provide the arch-shaped coupling element 540 with a textured surface, thereby facilitating better gripping of the device. Optionally, arch-shaped coupling element 540 may not include holes 502.

A proximal end 541 of the arch-shaped element 540 may be connected to a portion of the drill entry portion body 520, just proximal to the first gripping element 534, and a distal end 543 of the arch-shaped element 540 may be connected to a vertical support 280 of the bone securing portion 514. Alternatively, arch-shaped element 540 may be connected at any portion along the drill entry portion body 520, between the body distal end 526 and the body proximal end 528. Alternatively, any suitable connection element may be provided instead of arch-shaped element 540 for connecting the drill entry portion 512 and the bone securing portion 514 together and, in particular, for rigidly connecting the drill entry portion 512 and the bone securing portion 514 together. Optionally, arch-shaped element 540 may be coupled to the body 520 of the drill entry portion 512 and may be separated from body 520, by any suitable mechanism such as, for example, a snap-fit connection.

As discussed above with regard to the second embodiment of the invention, optionally, arch-shaped element 540 may be formed of two separate coupling portions (not shown) which allow the drill entry portion 512 and the bone securing portion 514 to move toward each other and to be locked in position when they are in engagement with the bone 2.

Arch-shaped element 540 may be optionally provided with a depending support member 242 for contacting skin adjacent a third side 3c of the bone, whereby support member 242 may be similar in structure and function to support member 142 described herein with regard to the second embodiment (FIG. 6A) and will not, therefore, be discussed here in further detail. As discussed herein, support member 242 may facilitate alignment of the drill entry portion 512 with the first side 3a of the bone 2.

Figure 19:
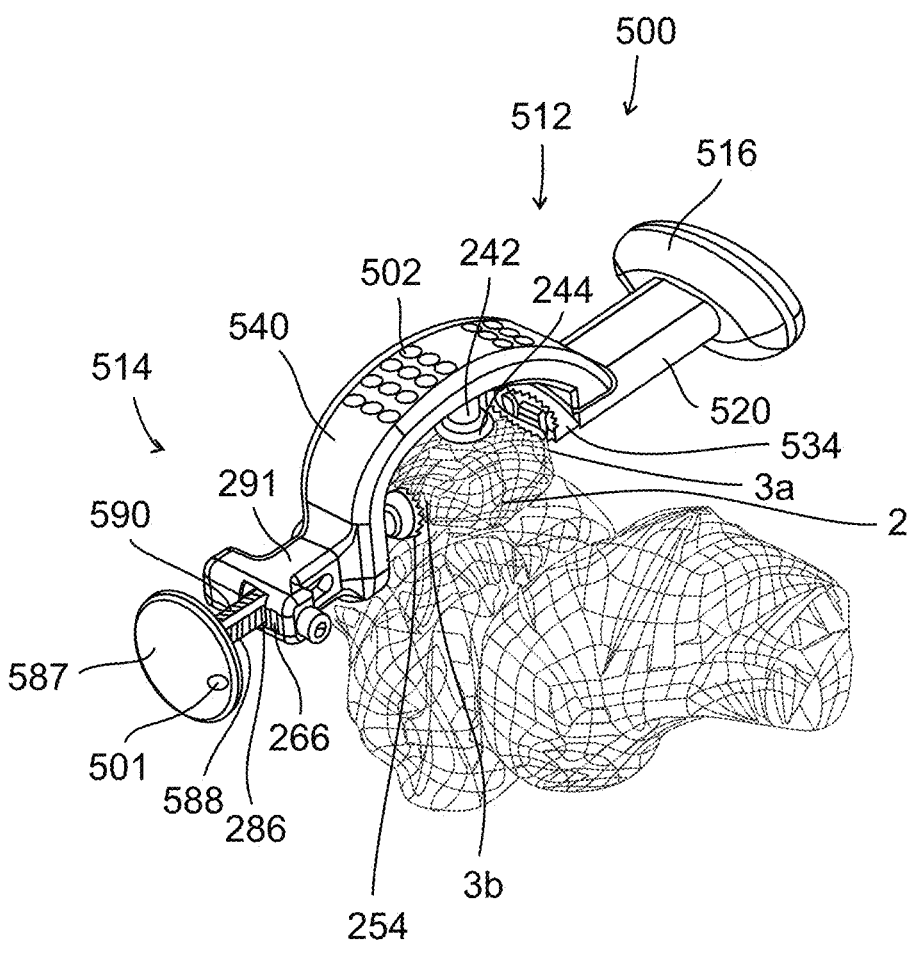
FIG. 19 is a perspective view of the device according to the fourth embodiment of the present invention, the device shown in engagement with a bone.

As noted above, bone securing portion 514 includes a vertical support 280 which extends downward from arch-shaped coupling element 540. Vertical support 280 may be provided with a bore 281 extending therethrough (FIG. 16C), from a distal side 282 to a proximal side 283 thereof, and the distal side 282 of vertical support 280 may be provided with an extension 291 having a bore 286 (FIG. 16D), similar to corresponding elements of device 200 (FIGS. 8A-D). As discussed herein with regard to device 200, bore 281 of vertical support 280 and bore 286 of extension 291 are aligned, and are sized and shaped to receive an adjustable fixation element 590 which differs in structure from fixation element (screw) 290 in device 200. Fixation element 590 is discussed further herein. A second gripping element 254 is connected to the fixation element 590, for engaging and gripping the second side 3b of a bone 2 (FIG. 19). Both second gripping element 254 and fixation element 590 may be positioned along an axis 594. Optionally, axis 594 may be parallel to the axis 522 of drill entry portion 512. Optionally, fixation element 590 and drill entry portion 512 are coaxial.

Second gripping element 254 is similar in structure and function to second gripping element 254 described herein with regard to device 200 and will not, therefore, be discussed here further.

Extension 291 may include finger grips 262 and 264, a slot 266, and an aperture 267 which are similar to corresponding elements discussed above with reference to device 200, and will not be described here in further detail. The function of these elements as part of device 500 is discussed further below.

With additional reference to FIGS. 18A-C, fixation element 590 includes a head portion 587 at a distal end 597 of the fixation element and a shank 588 extending along an axis 560 from the head portion to a proximal end 596 of the fixation element. Head portion 587 is preferably of a size and shape that facilitates easy gripping of the fixation element 590. For example, head portion 587 may be circular and/or may have a diameter of, for example, 36 mm and/or may have a thickness of, for example, 11 mm. It should, however, be noted that, if desired, any suitable size and shape of head portion 587 may be provided. Head portion 587 is provided with a marking 501, such as, for example, a painted dot or a hole or a depression, preferably located adjacent an outer periphery of head portion 587, which will be discussed further below. At least a portion of shank 588 is provided with a plurality of adjacent rings 599 which protrude radially outward from the shank. Each ring 599 includes a first portion 584 disposed at an angle relative to the shank, the angled portion 584 extending around a majority of the shank 588, and a second portion 585 which is parallel to shank axis 560. The rings 599 are assembled in an adjacent arrangement along the shank 588, with corresponding first portions 584 aligned and extending around a majority of the shank and corresponding second portions 585 arranged on the remaining portion of the shank. Additionally, second portions 585 are aligned on the side of shank 588 adjacent marking 501.

In order to assemble the components (FIG. 16D) of the bone securing portion 514, proximal end 596 of fixation element 590 may be inserted through bore 286 in extension 291 and through bore 281 in vertical support 280, such that the proximal end 596 of the fixation element extends through vertical support 280. The second gripping element 254 may be attached to the proximal end 596 of fixation element 590 by inserting the proximal end 596 into bore 255 in the second gripping element 254. Alternatively, proximal end 596 of fixation element 590 may be provided with a bore for insertion thereinto of the neck 253 of the second gripping element 254.

Once the bone securing portion 514 has been assembled, the fixation element 590 may be moved proximally or distally within bore 281 in vertical support 280 and bore 286 in extension 291. Movement of fixation element 590 proximally will result in a corresponding movement of the attached second gripping element 254 in a proximal direction, while movement of fixation element 590 distally will result in a corresponding movement of the attached second gripping element in a distal direction. These movements change a distance between first gripping element 534 and second gripping element 254, as discussed further herein.

As shown in FIGS. 16A-D, device 500 may be provided with a one-way locking mechanism 510 for maintaining the distance between the first gripping element 534 and the second gripping element 254. Optionally, locking mechanism 510 may include any type of ratchet mechanism, as known in the art. Specifically, in the embodiment shown, locking mechanism 510 includes a locking screw 312 and a locking element 302 which will not be described further here, as they are similar in structure and function to corresponding components shown in FIG. 10, regarding device 200.

With particular reference to FIG. 17, extension 291 includes a slot 266 for insertion thereinto of locking element 302, as described herein with regard to device 200. Locking element 302 may be inserted into slot 266 and advanced further into the interior of the extension 291 until second end 308 of locking element 302 engages rings 599, for example, rings 599a and 599b, between adjacent angled portions 584a and 584b (FIG. 18C). Locking screw 312 may then be inserted, as discussed above with regard to device 200, to retain locking element 302 in position within extension 291.

In order to prevent movement of the second gripping element 254 in a distal direction, fixation element 590 must be in a locked orientation, in which angled portions 584 of rings 599 are on the side of the extension 291 adjacent aperture 267. Since parallel portions 585 are aligned on the side of shank 588 having marking 501, turning head portion 587 so that marking 501 is at the side of the extension 291 furthest away from aperture 267 ensures that parallel portions 585 will be on the side of the extension 291 furthest away from the aperture 267 and that angled portions 584 will be on the side of the extension 291 nearest the aperture.

When in the locked orientation, movement of fixation element 590 in a distal direction, for example, by pulling on head portion 587 distally, is prevented by an angled portion, for example, angled portion 584a, which abuts second end 308 of the locking element 302.

When still in the locked orientation, movement of fixation element 590 in a proximal direction, for example, by pushing head portion 587 in a proximal direction, will cause the second gripping element 254 to move toward the first gripping element 534. Due to flexibility of the locking element 254, as the shank 588 is moved proximally, the locking element may bend slightly (or the angled portion 584b may deform slightly), and the second end 308 of the locking element may slide over angled portion 584b and move out of engagement with the space between rings 599a and 599b, move over angled portion 584b, and settle in the adjacent space between rings 599b and 599c. By continuing to move the fixation element 590 proximally, the second gripping element 254 may be moved a selected distance toward the first gripping element 534.

In order to release the shank 588 from the locking element 302, so that it may be moved distally, thereby moving the second gripping element 254 away from the first gripping element 534, the fixation element 590 must be in an unlocked orientation, in which it is turned such that marking 501 on head portion 587 is on the side of the extension 291 nearest the aperture 267. This ensures that the locking element 302 is disengaged from angled portions 584 of rings 599, and that the parallel portions 585 of rings 599 are on the side of extension 291 nearest the aperture 267. The locking element 302 is then allowed to slide over the parallel portion 585 of the shank, as much as desired, as the shank 588 is moved distally.

Prior to use, fixation element 590 may be rotated so that marking 501 indicates an unlocked orientation, in which the marking is disposed on the side of extension 291 nearest aperture 267. In this unlocked orientation, the fixation element 590 may be moved axially and distally, thereby enlarging a distance between teeth 257 of the second gripping element 254 and teeth 552 of the first gripping element 534. Fixation element 590 may be moved a sufficient amount to provide ample space for locating the bone 2 between the first gripping element 534 and the second gripping element 254. In order to tighten the first gripping element 534 and the second gripping element 254 relative to the bone and to retain the relative positions of the first gripping element 534 and the second gripping element 254, fixation element 590 may be rotated to the locked orientation, after which the fixation element may be moved proximally until locking element 302 engages angled portions 584 of shank 588, after which the fixation element may be moved proximally as desired, as discussed above.

In order to securely grip the bone 2, the device 500 may be positioned relative to bone 2 such that arch-shaped element 540 may be located above the bone, optionally with a support surface 244 of support member 242 in contact with skin adjacent a top surface 3c (FIG. 19) of the bone 2. The first gripping element 534 may be positioned adjacent the first side 3a of the bone 2. With head portion 587 in the locking orientation, fixation element 590 may then be moved proximally, thereby moving the second gripping element 254 toward the second side 3b of the bone 2.

As fixation element 590 is allowed to move proximally, as discussed above, the second gripping element 254 is allowed to be moved toward the first gripping element 534, Proximal movement of fixation element 590 is continued until second gripping element 254 engages skin adjacent the second side 3b of the bone 2.

Device 500 may be provided with a handle 516 which may be selectably connected to the drill entry portion 512, adjacent the body proximal end 528. Handle 516 may have any suitable shape which allows easy gripping of the device 500 during a surgical procedure. Optionally, handle 516 has an elliptical shape. For example, handle 516 may have an elliptical configuration with a long axis of approximately 45 mm and a short axis of approximately 20 mm. Optionally, handle 516 may resemble an automotive gear shift handle, thereby allowing easy gripping and moving of the device 500. Optionally, device 500 may include no handle on the drill entry portion 512.

The provision of a handle 516 which does not extend significantly below the channels 524 may provide the device 500 with a compact structure. For example, the entire device 500 may have a height, from the bottom of the vertical support 280 to the top of arch-shaped coupling element 540 (FIG. 16A) of approximately 57 mm. This compact design may allow easier maneuvering of the device 500 relative to a bone, as the handle itself does not interfere with the surgical site. In particular, due to the relatively small size of the handle 516, a surgeon may select any one of a number of orientations of the device relative to the bone, depending on the particular procedure to be performed, physical structure of the surgical site, and personal preference of the surgeon.

It should also be noted that handle 516 is shown, for example, in FIGS. 16A-C, as including upper and lower gripping surfaces 527 and 529, respectively located above and below the channels 524. Provision of gripping surfaces 527 and 529 may allow a surgeon to grip the device 500 at portions of the handle 516 above and below the channels 524, without interfering with insertion of a drill or other elements into the channel(s) 524.

It should be noted that, in the embodiment shown, the first and second gripping elements 534 and 254 provide at least three contact points between the device 500 and the bone 2 and/or skin adjacent the bone. The three contact points include at least one contact point between the drill entry portion 512 and the first side 3a of the bone 2 and at least one contact point between the bone securing portion 514 and skin adjacent the second side 3b of the bone 2. Additionally, as noted above, the optional support member 242 may provide further contact between the device 500 and the bone 2, specifically on skin adjacent the upper side 3c of the bone, which provides additional stability, thereby preventing relative movement between device 500 and the bone 2 during a surgical procedure, as discussed above.

However, as noted herein with regard to device 10 (FIGS. 2A-5C), device 500 may be specifically designed such that there are provided a minimum of three contact points between the device and the bone 2 (and/or skin adjacent the bone). The at least three contact points may include at least two contact points between the drill entry portion 512 and the bone first side 3a, for example, provided by first gripping element 534, and at least one contact point between the bone securing portion 514 and skin adjacent the bone second side 3b, provided by the second gripping element 254. Optionally, the first gripping element 534 may provide at least two contact points between the drill entry portion 512 and the bone first side 3a, the at least two contact points being spaced apart a distance of up to, for example, 25 mm, at opposite ends of the oval cross-sectional profile 235 (FIG. 17). Alternatively, in some embodiments, the at least three contact points may include at least one contact point between the drill entry portion 512 and the bone first side 3a, and at least two contact points between the bone securing portion 514 and skin adjacent the bone second side 3b. Optionally, the second gripping element 254 may provide at least two contact points between the bone securing portion 514 and the bone second side 3b, the at least two contact points being spaced apart a distance of up to, for example, 14 mm, at opposite sides of the second gripping element 254.

Provision of at least three contact points, located on at least two opposite sides of the bone 2 (and/or skin adjacent the bone) may provide the device 500 with stability relative to the bone, allowing the bone to be securely gripped during a surgical procedure such as, for example, drilling into the bone and/or anchor insertion, as discussed herein. Further contact points between the device 500 and the bone (and/or skin adjacent the bone), noted above, may provide further stability, as discussed herein.

It should be noted that many of the features of the various embodiments, while described only with respect to a particular embodiment or embodiments, may optionally be applied to any of the other embodiments. For example, a handle having multiple attachment locations relative to a drill entry portion, may be incorporated into the second embodiment (FIG. 6A), which is described herein as having a handle that may be rigidly connected to the drill entry portion or into the fourth embodiment (FIG. 16A). Similarly with other features such as, for example, the cup-shaped second gripping element of the third embodiment (FIG. 8A), this may be incorporated into the second embodiment (FIG. 6A).

Figure 11:
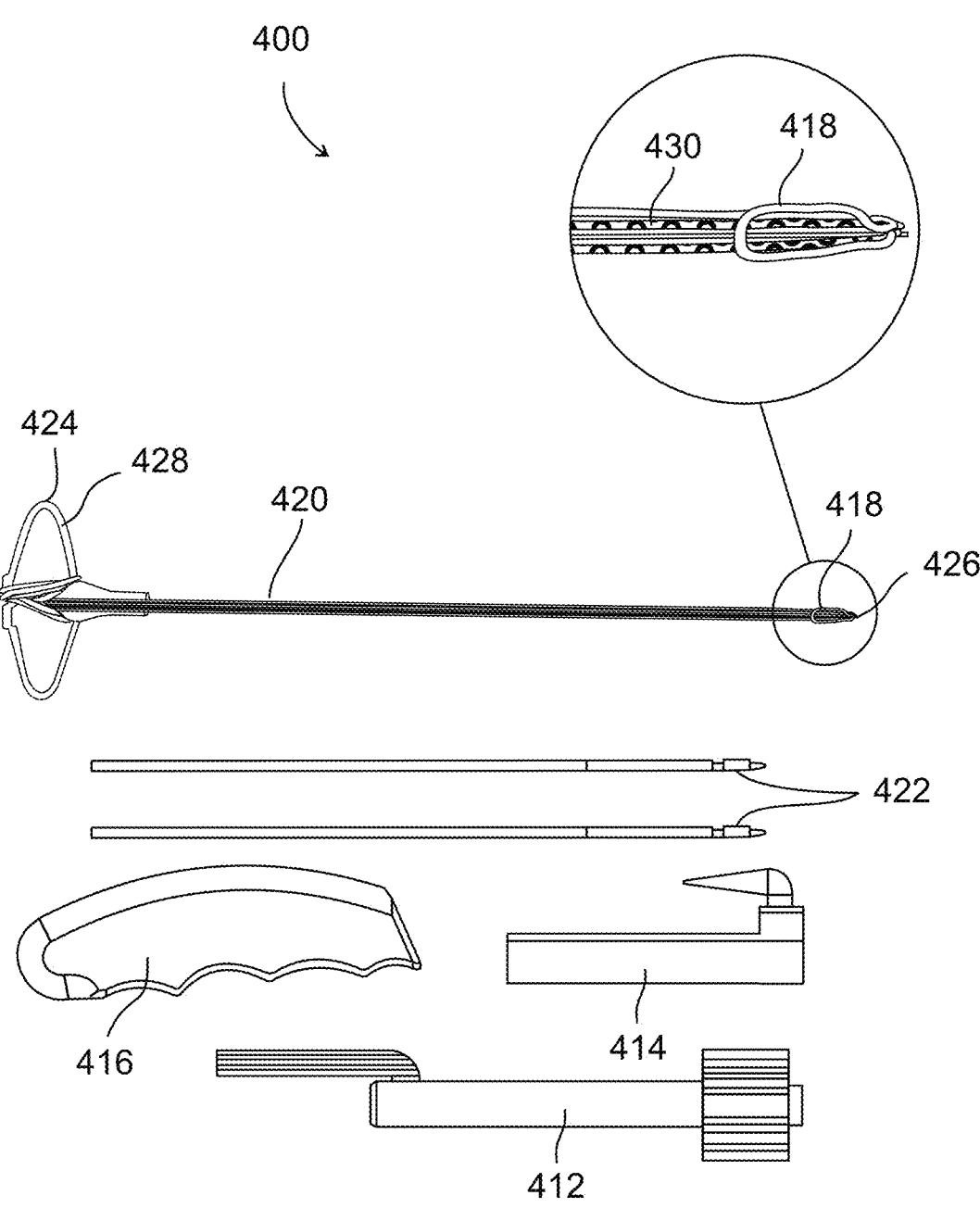
FIG. 11 is a side view of a kit including the device according to the first embodiment of the invention, with a portion of the kit shown enlarged for detail.

With additional reference to FIG. 11 there is shown a kit 400 in accordance with embodiments of the invention. Kit 400 includes a drill entry portion 412, a bone securing portion 414, and a handle 416 which may be assembled to form a guiding device as discussed herein such as, for example, guiding device 10. Kit 400 may also include at least one drill 422 for drilling a bore in a bone, the drill sized to be received in a drill guide of the drill entry portion 412. Optionally, the at least one drill 422 is suitable for drilling a bore in a bone, the bore having a diameter of from 0.1-10 mm. The kit 400 further includes an anchor inserter 420 having a proximal end 424 and a distal end 426. Anchor inserter proximal end 424 may be provided with a handle 428 to facilitate insertion of anchor(s) 418 into bore(s) drilled in the bone, as discussed in detail herein.

The kit further includes at least one anchor 418, the anchor sized to be received in a bore drilled by a drill 422. In embodiments, the anchor 418 may be a suture anchor and the anchor may be inserted by forcing it in to a bore in the bone. However, it should be noted that any type of anchor suitable for being inserted into a bore that has been drilled in a bone may be included in kit 400 such as, for example, but not limited to, a screw-in anchor, a deployable anchor, and a bioresorbable anchor. The at least one anchor 418 anchor may be fabricated of any suitable material, for example, suture material, titanium, stainless steel, PEEK (polyether ether ketone), or UHMWPE (ultra-high molecular weight polyethylene). In some embodiments, the anchor may optionally have an interference fit.

Each anchor 420 may be provided with a length of suture 430. Optionally, at least one anchor 420 may be preloaded onto anchor inserter 420. Optionally, at least one anchor 420 has an attached length of suture material 430. Optionally, anchor 420 having an attached length of suture may be preloaded onto anchor inserter 420.

Further, while kit 400 has been described with regard to the first embodiment, it should be noted that, alternatively, a guiding device in accordance with any of the described embodiments may be incorporated into the kit in accordance with the invention.

Figure 12A:
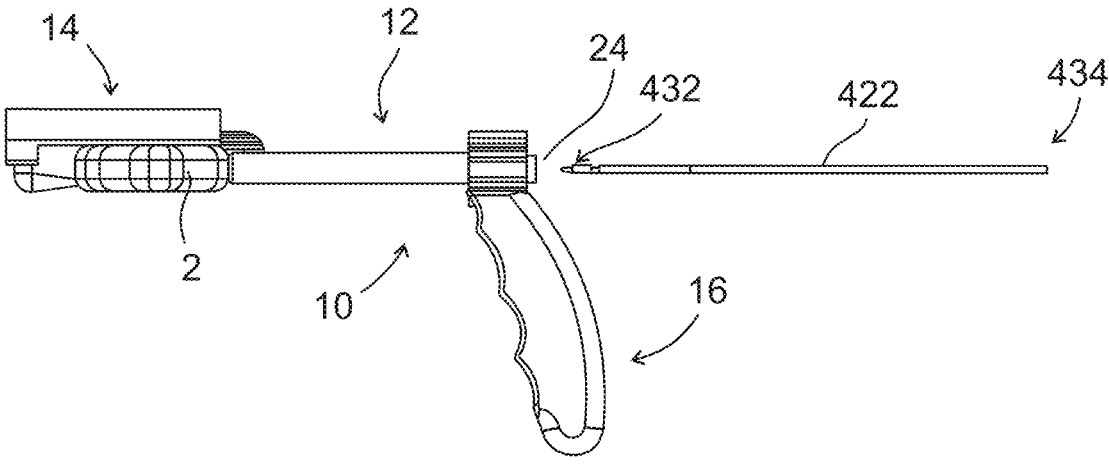
FIGS. 12A-B are respective side and perspective views of a device according to the first embodiment of the invention, the device shown prior to and during a drilling procedure, respectively.
Figure 12B:
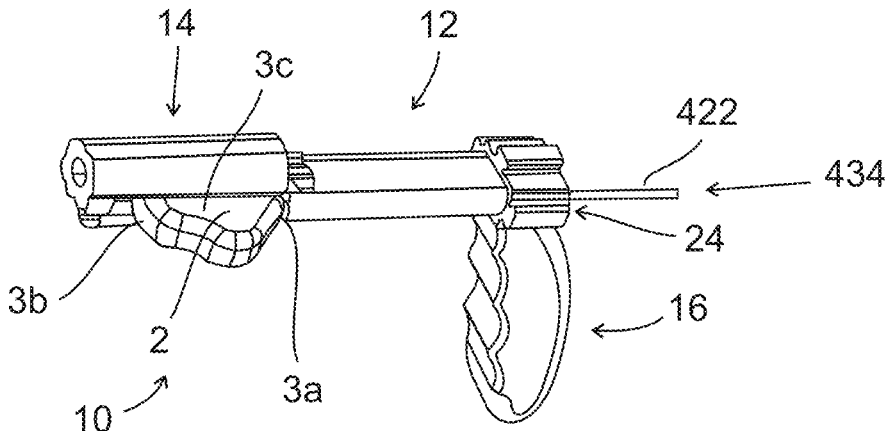

Referring now to FIGS. 12A-B there is shown device 10 according to embodiments of the invention, the device shown during a drilling procedure. Device 10 includes drill entry portion 12. Bone securing portion 14, and handle 16, these components shown assembled and in use while in engagement with a bone 2 such as, for example, a patella.

A drill 422 having a proximal end 434 and a distal end 432 is shown in FIG. 12A prior to being inserted into a channel 24 in drill entry portion 12, as discussed hereinabove with regard to the first embodiment of the invention.

FIG. 12B shows the drill 422 having already been inserted into channel 24, with distal end 432 of drill 422 in contact with bone 2. It should be noted that, due to the configuration of the bone 2, which includes first and second opposite sides 3a and 3b and a generally flat upper side 3c, drilling may be performed at a substantially horizontal orientation relative to a plane (not shown) of the bone. This may be facilitated by providing a device 10 having at least one channel 24 parallel to the device longitudinal axis, the channels engaging a first side of the bone. This may further be facilitated by providing bone securing portion 14 wherein portions which engage a second side of the bone are disposed along an axis parallel to the device longitudinal axis (see FIGS. 2B and 4A). Further, coupling of the drill entry portion 12 with the bone securing portion 14 may be along an axis parallel to the device longitudinal axis, and contact of a portion of the bone securing portion 14 included in the coupling with an upper side 3c of the bone, as discussed herein and shown in FIGS. 12A-B, further provides stability to this orientation of device 10 relative to the bone, as discussed herein.

While the feature whereby drilling may be performed in a generally horizontal orientation relative to a plane of the bone is shown in FIGS. 12A-B, it should also be noted that this feature may be also relevant regarding other embodiments of the invention discussed herein.

Figure 13A:
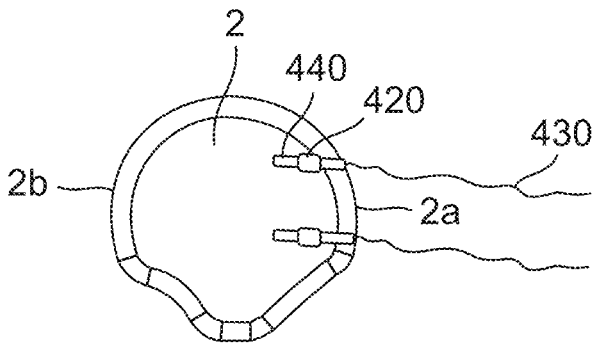
FIGS. 13A-B are respective side and perspective views of a bone having anchors inserted therein, in accordance with embodiments of the invention.
Figure 13B:
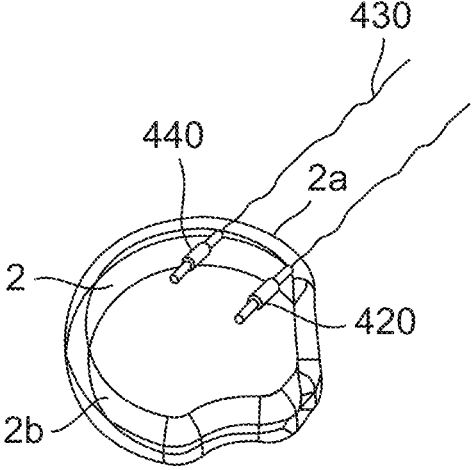

Referring now to FIGS. 13A-B, a bone 2 is shown during a procedure to insert anchors therein. It should be noted that a pair of bores 440 has been drilled in the anchor, the bores drilled on a first side 3a of the bone 2.

It should also be noted that the bores 440 are parallel, having been drilled using, for example, the device shown in FIGS. 12A-B, where each bore was drilled using one of the two parallel channels 24. Further, it should be noted that the bores 440 were each drilled into bone 22 a preselected same distance, optionally using a measurement indicator provided on the drill, as known in the art.

Figure 14:
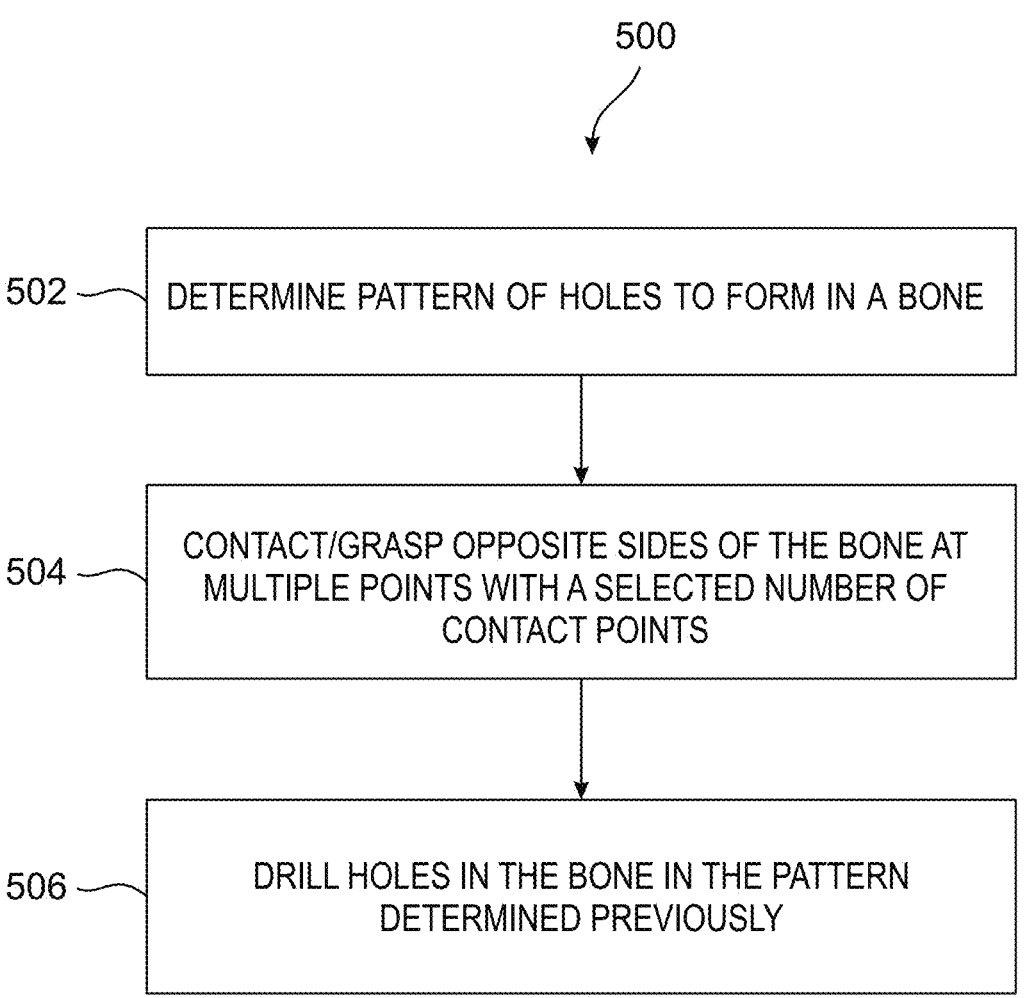
FIG. 14 is a flowchart illustrating the main actions performed by a surgeon during a procedure including forming at least one bore in a bone, in accordance with embodiments of the invention.

With reference to FIG. 14 there is shown a flowchart illustrating actions of a method 500 for drilling bores in a bone, in accordance with embodiments of the invention. Method 500 may be performed by a surgeon using a bone drill guiding device in accordance with any of the embodiments of the invention, the method 500 performed during a procedure including forming at least one bore in a bone.

According to method 500, at 502, a surgeon determines a pattern of bores to form in a bone. At 504, opposite sides of the bone are contacted at multiple contact points of a bone drill guiding device to securely engage and grip the bone at the multiple contact points. The contact point(s) of a drill entry portion of the device with a first side of the bone may be provided on cannula(s) of the drill entry portion. The device also includes a bone securing portion which includes at least one contact point for securely engaging and gripping the second side of the bone, opposite the first side, via skin adjacent the second side of the bone. As discussed herein, the multiple contact points include at least one contact point on a first side of the bone and at least one contact point on a second side of the bone. At 506, bores are drilled in the bone, according to the pattern determined in action 502.

Figure 15C:
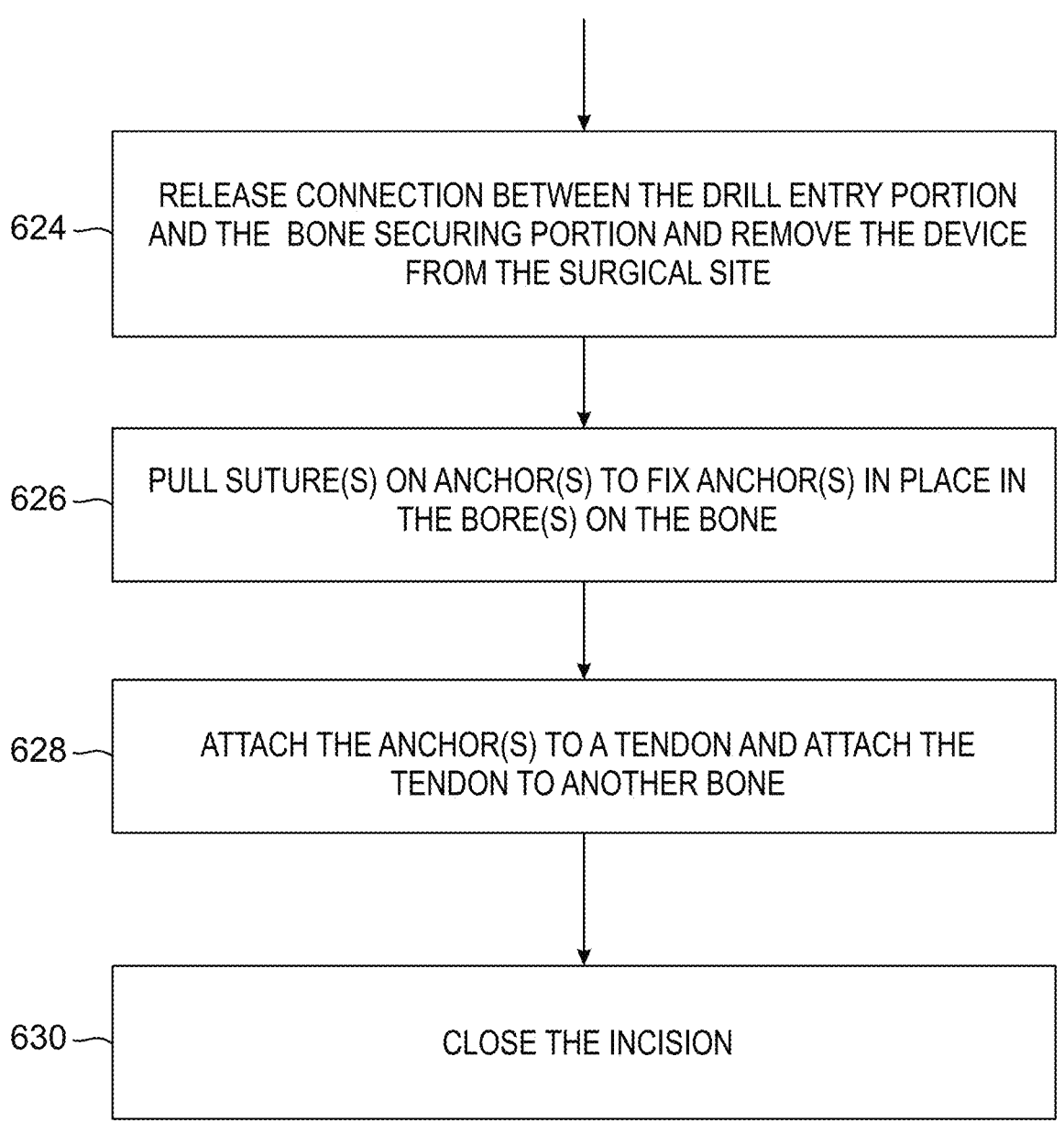

With reference to FIGS. 15A-C there is shown a flowchart illustrating, in more detail, actions of a method 600 for drilling bores in a bone, in accordance with embodiments of the invention. Method 600 may be performed by a surgeon using any of the devices in accordance with embodiments of the invention, the method 600 performed during a procedure including forming at least one bore in a bone.

According to method 600, at 602, a surgeon determines a first side of a bone for insertion of at least one anchor therein.

At 604, an incision may be made in skin adjacent the first side of the bone, in order to access the first side of the bone. A typical incision may be, for example, 22 mm, although a larger incision such as, for example, 25 mm, may be made in certain cases such as, for example, if it is difficult to position the device properly on the patella.

Optionally, at 605, a third side of the bone may be contacted with a support member, to align a drill entry portion of the device with the first side of the bone. At 606, a drill entry portion of a bone drill guiding device may be positioned on the first side of the bone, with the aid of the support member for aligning the drill entry portion on the first side of the bone. The drill entry portion includes at least a first contact point to engage and grip the first side of the bone, as discussed hereinabove. At 608, at least a component of a bone securing portion the bone drill guiding device may be positioned on a second side of the bone, opposite the first side. The component includes at least a second contact point to engage and grip the second side of the bone, via the adjacent skin.

At 610, in accordance with some embodiments, the drill entry portion and at least the component of the bone securing portion are rigidly connected on respective first and second sides of the bone such that at least a third contact point, on the drill entry portion or the bone securing portion engages the first side of the bone or skin adjacent the second side of the bone, respectively. Optionally, the drill entry portion and the bone securing portion may be rigidly connected to each other by sliding them axially toward each other, as discussed herein with regard to the first embodiment of the bone drill guiding device in accordance with the invention. Optionally, the drill entry portion and the bone securing portion are slid toward each other along an axis parallel to a longitudinal axis of the device. Optionally, the rigid connection between the drill entry portion and the bone securing portion may include a ratchet mechanism.

Alternatively, according to some embodiments, the drill entry portion and the bone securing portion are rigidly positioned relative to each other by moving the component proximally to engage the second side of the bone, or skin adjacent the second side of the bone. Optionally, a locking mechanism may be used to lock the position of the component relative to the drill entry portion.

At 612, a drill may be inserted into a first channel in the drill entry portion, and the drill may be advanced distally until it contacts the first side of the bone. At 614, the drill advances into the bone to form a first bore in the bone. Optionally, the length of the bore in the bone may be measured, for example, by marking the drill when it first contacts the bone, at 612 and then measuring the distance the drill has been advanced into the bone. Alternatively, the drill may include markings which may indicate the length of the bore drilled in the bone. At 616, the drill may be operated in a reverse direction to actuate lateral/radial extension of at least one blade relative to the drill longitudinal axis, and a portion of the bore in the bone may be widened. At 618, the drill may be operated and advanced distally, to close the blade, and then the drill may be removed from the first channel in the drill entry portion at 620.

At 622, an anchor inserter may be used to insert an anchor through the first channel and into the first bore that was formed in the bone. A hammer tap on the proximal end of the anchor inserter may facilitate insertion of the anchor and its anchoring in the bore of the bore.

If it is desired to drill a second bore and insert a second anchor in the bone, actions 612, 614, 616, 618, 620, and 622 may be repeated to drill a second bore in the bone and insert a second anchor in the second bore. Alternatively, after performing actions 612, 614, 616, 618, 620 to form a first bore, these five action may be repeated to form a second bore in the bone, after which action 622 may be performed twice, once to insert a first anchor in the first bore and once to insert a second anchor in the second bore.

At 624, in accordance with some embodiments, after the anchor(s) have been inserted into the bore(s) formed in the bone, the device may be removed from the surgical site by releasing the rigid connection between the drill entry portion and the bone securing portion, after which the device may be released from engagement with the bone and removed from the surgical site. Alternatively, in accordance with some embodiments, the device may be removed from the surgical site by moving the component of the bone securing portion distally, thereby releasing engagement of the device from the bone at the contact points.

At 626, suture(s) attached to the anchor(s) may be pulled, which fixes the anchor(s) in place in the respective bore(s) in the bone. The surgical procedure continues at 628, for example, by attaching the anchor(s) to a tendon and attaching the tendon to another bone. Finally, at 630, the incision may be closed at the surgical site.

It is expected that during the life of a patent maturing from this application many relevant drill guide devices will be developed and the scope of the term offset guiding device is intended to include all such new technologies a priori.

As used herein, the offset guiding device is shown and described as being adapted to engage a patella and to guide a drill during a drilling procedure for drilling a bore in the patella. However, it should be noted that the device may, alternatively, be utilized to securely engage any other bone and guide a drill for drilling a bore in the bone, as long as the bone is of a suitable size and shape for being securely engaged by the device.

The terms "comprises," "comprising," "includes," "including," "having" and their conjugates mean "including but not limited to."

The term "consisting of" means "including and limited to."

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A bone drill guiding device, comprising:
   a drill entry portion including a first contact point for engaging a first side of a bone, wherein said drill entry portion includes at least one bore sized to receive a bone drill therethrough;
   a bone securing portion including a second contact point for engaging a second side of the bone, the second side of the bone opposite the first side of the bone;
   wherein said device includes a third contact point on said bone securing portion;
   a coupling to selectably rigidly connect said drill entry portion and said bone securing portion for positioning said drill entry portion and said bone securing portion on opposite sides of the bone; and
   an adjustable fixation element, wherein said second contact point is defined by a proximal point of the adjustable fixation element, said fixation element movable axially and proximally relative to said bone securing portion to engage the second side of the bone, said fixation element movable axially and distally relative to said bone securing portion to release the second side of the bone from the bone securing portion;
   wherein said adjustable fixation element includes:
      a screw thread rotatable in a first direction to move said fixation element proximally relative to said bone securing portion and rotatable in a second direction opposite to said first direction to move said fixation element distally relative to said bone securing portion; and
      a lock configured to engage said screw thread for retaining said adjustable fixation element at an extended or retracted position.

2. The bone drill guiding device according to claim 1, wherein at least one of:
   said drill entry portion includes said first contact point for engaging the first side of the bone through intermediate tissue; and
   said bone securing portion includes said second contact point for engaging the second side of the bone through intermediate tissue.

3. The bone drill guiding device according to claim 1, wherein said device has a longitudinal axis and wherein said drill entry portion comprises a plurality of channels, each said channel sized to receive the bone drill therethrough and each said channel having a longitudinal axis at a preselected orientation relative to said device longitudinal axis.

4. The bone drill guiding device according to claim 3, wherein said longitudinal axes of said channels are spaced apart by about 5 mm.

5. The bone drill guiding device according to claim 3, wherein said drill entry portion includes first and second channels;
   wherein said drill entry portion includes first and second distally extending contact portions adjacent said first and second channels, respectively, said first and second distally extending contact portions defining said first and third contact points, respectively;
   said bone drill guiding device further including a third distally extending contact portion that extends out of said drill entry portion, wherein said first, second, and third distally extending contact portions define an isosceles triangle with a base at said first and second distal contact portions.

6. The bone drill guiding device according to claim 5, wherein said third distal contact portion is configured to contact a third side of the bone, said third side of the bone between the first and second sides.

7. The bone drill guiding device according to claim 1, wherein said coupling includes a stabilizing portion configured to contact skin adjacent an upper surface of the bone between said drill entry portion and said bone securing portion.

8. The bone drill guiding device according to claim 7, wherein said stabilizing portion is configured to be extendible from said coupling to contact the skin adjacent the upper surface of the bone.

9. The bone drill guiding device according to claim 1, wherein at least one of:

(a) said bone securing portion includes an open ended portion directed proximally, said open ended portion of said bone securing portion including a plurality of contact points for contacting the second side of the bone; and (b) said drill entry portion includes an open-ended portion positioned around said at least one bore, said open-ended portion of said drill entry portion having an open end directed distally, said open end including a plurality of contact points for contacting the first side of the bone;

wherein first and second ones of said plurality of contact points include said first contact point and said third contact point; and wherein said first and second ones of said plurality of contact points are farther apart than twice the diameter of said at least one bore.

10. The bone drill guiding device according to claim 1, wherein said drill entry portion includes a gripping portion, said gripping portion including said first and third contact points, and wherein said gripping portion includes a concave surface including said first and third contact points.

11. The bone drill guiding device according to claim 1, wherein said bone securing portion has a proximal end, said bone securing portion proximal end including said third contact point;

wherein said bone securing portion proximal end includes two fixation tips, wherein said second and third contact point are at the most proximal portions of said fixation tips; and wherein said drill entry portion includes a fourth contact point to engage the first side of the bone.

12. The bone drill guiding device according to claim 11, wherein said first, second, third, and fourth contact points are disposed in a single plane and define a quadrilateral with at least one pair of parallel sides, between said first and fourth contact points, and between said second and third contact points, respectively.

13. The bone drill guiding device according to claim 1, wherein said drill entry portion includes a distally-extending marker configured to provide alignment between said device and said bone.

14. The bone drill guiding device according to claim 13, wherein said marker is configured to provide a tactile marking in the bone.

15. The bone drill guiding device according to claim 13, wherein said marker is configured as one of a dot, a circle, a cross, and an X, said marker configured to provide said tactile marking as the said one of a dot, a circle, a cross, and an X.

16. The bone drill guiding device according to claim 1, further including a handle connectable to said drill entry portion at a selected one of a plurality of sides of said drill entry portion.

17. A method of drilling a bore in bone comprising:

positioning a drill entry portion of a bone drill guiding device on a first side of a bone, wherein said drill entry portion includes at least one bore sized to receive a bone drill therethrough;

positioning a bone securing portion on a second side of the bone, the second side of the bone opposite the first side of the bone;

moving the drill entry portion and the bone securing portion toward each other until at least a first contact point of the drill entry portion engages the first side of the bone and at least a second contact point and a third contact point of the bone securing portion engage the second side of the bone, wherein the drill entry portion and the bone securing portion collectively contact the bone at least three points including said first, second, and third contact points;

wherein said moving includes rotating a screw of an adjustable fixation element in a first direction to move the adjustable fixation element axially and proximally relative to the bone securing portion, said adjustable fixation element including a lock which engages a thread of the screw to retain the adjustable fixation element at an extended or retracted position;

inserting a drill into a proximal end portion of the drill entry portion until it contacts the bone; and drilling a bore a preselected distance in the bone with the drill.

18. The method according to claim 17, wherein said engaging includes said drill entry portion contacting the bone at at least one point on the first side of the bone and said bone securing portion contacting the bone at at least two points on the second side of the bone.

19. The method according to claim 17, wherein said drill entry portion includes a handle that is selectively connectable to said drill entry portion at one of multiple locations radially spaced around said bore, said method further including, before said drilling:

selecting one of said multiple locations at which to connect the handle; and connecting the handle to the drill entry portion at the selected location.

* * * * *